United States Patent [19]
Toothman et al.

[11] Patent Number: 5,731,144
[45] Date of Patent: Mar. 24, 1998

[54] HIGH AFFINITY TGFβ NUCLEIC ACID LIGANDS

[75] Inventors: Penelope J. Toothman, Boulder; Steven Ringquist, Lyons; Larry Gold, Boulder, all of Colo.

[73] Assignee: NeXstar Pharmaceuticals, Inc., Boulder, Colo.

[21] Appl. No.: 458,423

[22] Filed: Jun. 2, 1995

Related U.S. Application Data

[63] Continuation-in-part of Ser. No. 714,131, Jun. 10, 1991, Pat. No. 5,475,096, Ser. No. 931,473, Aug. 17, 1992, Pat. No. 5,270,163, Ser. No. 964,624, Oct. 21, 1992, Pat. No. 5,496,938, and Ser. No. 117,991, Sep. 8, 1993, said Ser. No. 714,131, is a continuation-in-part of Ser. No. 536,428, Jun. 11, 1990, abandoned.

[51] Int. Cl.⁶ ............... C12P 19/34; C12Q 1/68; C07H 21/04; C07H 21/02
[52] U.S. Cl. ............... 435/6; 435/91.2; 536/25.4
[58] Field of Search ............ 435/6, 92.1; 514/44; 935/77, 78

[56] References Cited

U.S. PATENT DOCUMENTS 5,270,163  12/1993  Gold et al.
5,459,015  10/1995  Janjic et al. .................... 435/6

FOREIGN PATENT DOCUMENTS 2 183 661   6/1987   United Kingdom .
WO 89/06694 7/1989   WIPO .
9214843     9/1992   WIPO .................... 435/6

OTHER PUBLICATIONS

Arteaga et al. (1993) J. Clin. Invest. 92:2569.
Arteaga et al. (1990) Cell Growth & Differentiation 1:367.
Barral et al. (1993) Proc. Natl. Acad. Sci. USA 90:3442.
Shah et al. (1992) Lancet 339:213.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY. p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to TGFβ. Included in the invention are specific RNA and ssDNA ligands to TGFβ1 identified by the SELEX method. Also included are RNA ligands that inhibit the interaction of TGFβ1 with its receptor.

9 Claims, 2 Drawing Sheets

HIGH AFFINITY TGFβ NUCLEIC ACID LIGANDS

RELATED APPLICATIONS

This application is a Continuation-in-Part of U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now issued as U.S. Pat. No. 5,270,163, U.S. patent application Ser. No. 07/964,624, filed Oct. 21, 1992, entitled Methods of Producing Nucleic Acid Ligands, now U.S. Pat. No. 5,496,938, and U.S. patent application Ser. No. 08/117,991, filed Sept. 8, 1993, abandoned, entitled High-Affinity Nucleic Acid Ligands Containing Modified Nucleotides. U.S. patent application Ser. No. 07/714,131 (now U.S. Pat. No. 5,475,096) is a Continuation-in-Part of U.S. patent application Ser. No. 07/536,428, filed Jun. 11, 1990, entitled Systematic Evolution of Ligands by EXponential Enrichment, now abandoned.

FIELD OF THE INVENTION

Described herein are methods for identifying and preparing high-affinity nucleic acid ligands to TGFβ. The method utilized herein for identifying such nucleic acid ligands is called SELEX, an acronym for Systematic Evolution of Ligands by EXponential enrichment. This invention includes high affinity nucleic acid ligands of TGFβ. Further disclosed are RNA and DNA ligands to TGFβ1. Also included are oligonucleotides containing nucleotide derivatives chemically modified at the 2'- positions of pyrimidines. Additionally disclosed are RNA ligands to TGFβ1 containing 2'-NH$_2$-modifications or 2'-F-modifications. This invention also includes high affinity nucleic acid inhibitors of TGFβ1. The oligonucleotides of the present invention are useful as pharmaceuticals or diagnostic agents.

BACKGROUND OF THE INVENTION

The transforming growth factor -β (TGFβ) polypeptides influence growth, differentiation, and gene expression in many cell types. The first polypeptide of this family that was characterized, TGFβ1 has two identical 112 amine acid subunits which are covalently linked. TGFβ1 is a highly conserved protein with only a single amine acid difference distinguishing humans from mice. There are two other members of the TGFβ gene family that are expressed in mammals. TGFβ2 is 71% homologous to TGFβ1(de Martin et al. (1987) EMBO J. 6:3673-3677), whereas TGFβ3 is 80% homologous to TGFβ1(Derynck et al. (1988) EMBO J 7:3737-3743). The structural characteristics of TGFβ1 as determined by nuclear magnetic resonance (Archer et al. (1993) Biochemistry 32:1164-1171) agree with the crystal structure of TGFβ2(Daopin et al. (1992) Science 257:369-374; Schlunegger and Grutter (1992) Nature 358:430-434).

Even though the TGFβ's have similar three dimensional structures, they are by no means physiologically equivalent. There are at least three different extracellular receptors, type I, II and III, involved in transmembrane signaling of TGFβ to cells carrying the receptors. For reviews, see Derynck (1994) TIBS 19:548-553 and Massague (1990) Annu. Rev. Cell Biol 6:597-641). In order for TGFβ2 to effectively interact with the type II TGFβ receptor, the type III receptor must also be present (Derynck (1994) TIBS 19:548-553). Vascular endothelial cells lack the type III receptor. Instead endothelial cells express a structurally related protein called endoglin (Cheifetz, et al. (1992) J. Biol. Chem. 267:19027-19030), which only binds TGFβ1 and TGFβ3 with high affinity. Thus, the relative potency of the TGFβ's reflect the type of receptor expressed in a cell and organ system.

In addition to the regulation of the components in the multifactorial signaling pathway, the distribution of the synthesis of TGFβ polypeptides also affects physiological function. The distribution of TGFβ2 and TGFβ3 is more limited (Derynck et al. (1988) EMBO J 7:3737-3743) than TGFβ1, eg. TGFβ3 is limited to tissues of mesenchymal origin, whereas TGFβ1 is present in both mesenchymal and epithelial cells.

TGFβ1 is a multifunctional cytokine critical for tissue repair. High concentrations of TGFβ1 are delivered to the site of injury by platelet granules (Assoian and Sporn, (1986) J Cell Biol. 102:1217-1223). TGFβ1 initiates a series of events that promote healing including chemotaxis of cells such as leukocytes, monocytes and fibroblasts, and regulation of growth factors and cytokines involved in angiogenesis, cell division associated with tissue repair and inflammatory responses. TGFβ1 also stimulates the synthesis of extracellular matrix components (Roberts et al., (1986) Proc. Natl. Acad Sci USA 83:4167-4171; Sporn et al., (1983) Science 219:1329-1330; Massague, (1987) Cell 49:437-438) and most importantly for understanding the pathophysiology of TGFβ1. TGFβ1 autoregulates its own synthesis (Kim et al., (1989) J Biol Chem 264:7041-7045).

A number of diseases have been associated with TGFβ1 overproduction. Fibrotic diseases associated with TGFβ1 overproduction can be divided into chronic conditions such as fibrosis of kidney, lung and liver and more acute conditions such as dermal scarring and restenosis. Synthesis and secretion of TGFβ1 by tumor cells can also lead to immune suppression such as seen in patients with aggressive brain or breast tumors (Arteaga et al., (1993) J Clin Invest 92:2569-2576). The course of Leishmanial infection in mice is drastically altered by TGFβ1 (Barral-Netto, et al. (1992) Science 257:545-547). TGFβ1 exacerbated the disease, whereas TGFβ1 antibodies halted the progression of the disease in genetically susceptible mice. Genetically resistant mice became susceptible to Leshmanial infection upon administration of TGFβ1.

The profound effects of TGFβ1 on extracellular matrix deposition have been reviewed (Rocco and Ziyadeh, (1991) in Contemporary Issues in Nephrology v23, Hormones, autocoids and the kidney. ed. Jay Stein, Churchill Livingston, NY pp391-410; Roberts et al., (1988) Rec. Prog. Hormone Res. 44:157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGFβ1 has profound effects on the kidney. The accumulation of mesangial matrix in proliferative glomerulonephritus (Border et al., (1990) Kidney Int. 37:689-695) and diabetic nephropathy (Mauer et al., (1984) J. Clin Invest.74:1143-1155) are clear and dominant pathological features of the diseases. TGFβ1 levels are elevated in human diabetic glomerulosclerosis (advanced neuropathy) (Yamamoto et al., (1993) Proc. Natl. Acad. Sci. 90:1814-1818). TGFβ1 is an important mediator in the genesis of renal fibrosis in a number of animal models (Phan (et al.), (1990) Kidney Int. 37:426; Okuda et al., (1990) J. Clin Invest. 86:453). Suppression of experimentally induced glomerulonephritus in rats has been demonstrated by anti-serum against TGFβ1 (Border et al., (1990) Nature 346:371) and by an extracellular matrix protein, decorin, which can bind TGFβ1 (Border et al., (1992) Nature 360:361–363).

Too much TGFβ1 leads to dermal scar-tissue formation. Neutralizing TGFβ1 antibodies injected into the margins of healing wounds in rats have been shown to inhibit scarring without interfering with the rate of wound healing or the tensile strength of the wound (Shah et al., (1992) Lancet 339:213–214). At the same time there was reduced angiogenesis, reduced number of macrophages and monocytes in the wound, and a reduced amount of disorganized collagen fiber deposition in the scar tissue.

TGFβ1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGFβ1 gene, TGFβ1 gene expression was associated with both extracellular matrix synthesis and hyperplasia (Nabel et al., (1993) Proc. Natl. Acad. Sci USA 90:10759–10763). The TGFβ1 induced hyperplasia was not as extensive as that induced with PDGF-BB, but the extracellular matrix was more extensive with TGFβ1 transfectants. No extracellular matrix deposition was associated with FGF-1 (a secreted form of FGF) induced hyperplasia in this gene transfer pig model (Nabel (1993) Nature 362:844–846).

There are several types of cancer where TGFβ1 produced by the tumor may be deleterious. MATLyLu rat cancer cells (Steiner and Barrack, (1992) Mol. Endocrinol. 6:15–25) and MCF-7 human breast cancer cells (Arteaga et al (1993) Cell Growth and Differ. 4:193–201) became more tumorigenic and metastatic after transfection with a vector expressing the mouse TGFβ1. In breast cancer, poor prognosis is associated with elevated TGFβ (Dickson et al., (1987) Proc. Natl. Aced Sci. USA 84:837–841; Kasid et al., (1987) Cancer Res. 47:5733–5738; Daly et al., (1990) J Cell Biochem 43:199–211; Barrett-Lee et al., (1990) Br. J Cancer 61:612–617; King et al., (1989) J Steroid Biochem 34:133–138; Welch et al., (1990) Proc. Nat. Acad Sci. 87:7678–7682; Walker et al (1992) Eur J Cancer 238:641–644) and induction of TGFβ1 by tamoxifen treatment (Butta et al, (1992) Cancer Res 52:4261–4264) has been associated with failure of tamoxifen treatment for breast cancer (Thompson et al, (1991) Br. J Cancer 63:609–614). Anti TGFβ1 antibodies inhibit the growth of MDA-23 1 human breast cancer cells in athymic mice (Arteaga et al., (1993) J Clin Invest 92:2569–2576), a treatment which is correlated with an increase in spleen natural killer cell activity. CHO cells transfected with latent TGFβ1 also showed decreased NK activity and increased tumor growth in nude mice (Wallick et al., (1990) J Exp Med 172:1777–1784). Thus, TGFβ1 secreted by breast tumors may cause an endocrine immune suppression.

High plasma concentrations of TGFβ1 have been shown to indicate poor prognosis for advanced breast cancer patients (Anscher, et al. (1993) N Engl J Med 328:1592–8). Patients with high circulating TGFβ before high dose chemotherapy and autologous bone marrow transplantation are at nigh risk for hepatic veno-occlusive disease (15–50% of all patients with a mortality rate up to 50%) and idiopathic interstitial pneumonitis (40–60% of all patients). The implication of these findings is 1) that elevated plasma levels of TGFβ1 can be used to identify at risk patients and 2) that reduction of TGFβ1 could decrease the morbidity and mortality of these common treatments for breast cancer patients.

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Pat. No. 5,270,163 (see also WO 91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed "counter-SELEX." U.S. patent application Ser. No. 08/143, 564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No.

08/117,991, filed Sep. 8, 1993, entitled High Affinity Nucleic Acid Ligands Containing Modified Nucleotides, that describes oligonucleotides containing nucleotide derivatives chemically modified at the 5- and 2'-modifications of pyrimidines, as well as specific RNA ligands to thrombin containing 2'-amino modifications. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). Each of these applications is specifically incorporated herein by reference.

BRIEF SUMMARY OF THE INVENTION

The present invention includes methods of identifying and producing nucleic acid ligands to transforming growth factor beta (TGFβ) and the nucleic acid ligands so identified and produced. For the purpose of this application, TGFβ includes human TGFβ1, TGFβ2, and TGFβ3 and TGFβ's that are substantially homologous thereto. By substantially homologous it is meant a degree of amino acid sequence identity of 70% or more. In particular, RNA sequences are provided that are capable of binding specifically to TGFβ1. Specifically included in the invention are the RNA ligand sequences shown in Table 3 (SEQ ID NOS:12–42). These RNA ligand sequences include both pre and post SELEX modifications as shown in Table 2. Also included in this invention are RNA ligands of TGFβ1 that inhibit the function of TGFβ1.

Also included in the invention are ssDNA ligands to TGFβ1. Specifically included in the invention are the ssDNA ligand sequences shown in Table 6 (SEQ ID NOS:55–89).

Further included in this invention is a method of identifying nucleic acid ligands and nucleic acid ligand sequences to TGFβ comprising the steps of (a) preparing a candidate mixture of nucleic acids, (b) contacting the candidate mixture of nucleic acids with TGFβ, (c) partitioning between members of said candidate mixture on the basis of affinity to TGFβ, and (d) amplifying the selected molecules to yield a mixture of nucleic acids enriched for nucleic acid sequences with a relatively higher affinity for binding to TGFβ.

More specifically, the present invention includes the RNA and ssDNA ligands to TGFβ identified according to the above-described method, including those ligands shown in Tables 3 and 6 (SEQ ID NOS: 12–42; 55–89). Also included are nucleic acid ligands to TGFβ that are substantially homologous to any of the given ligands and that have substantially the same ability to bind TGFβ and inhibit the function of TGFβ. Further included in this invention are nucleic acid ligands to TGFβ that have substantially the same structural form as the ligands presented herein and that have substantially the same ability to bind TGFβ and inhibit the function of TGFβ.

The present invention also includes other modified nucleotide sequences based on the nucleic acid ligands identified herein and mixtures of the same.

DETAILED DESCRIPTION OF THE INVENTION

Figure 1:
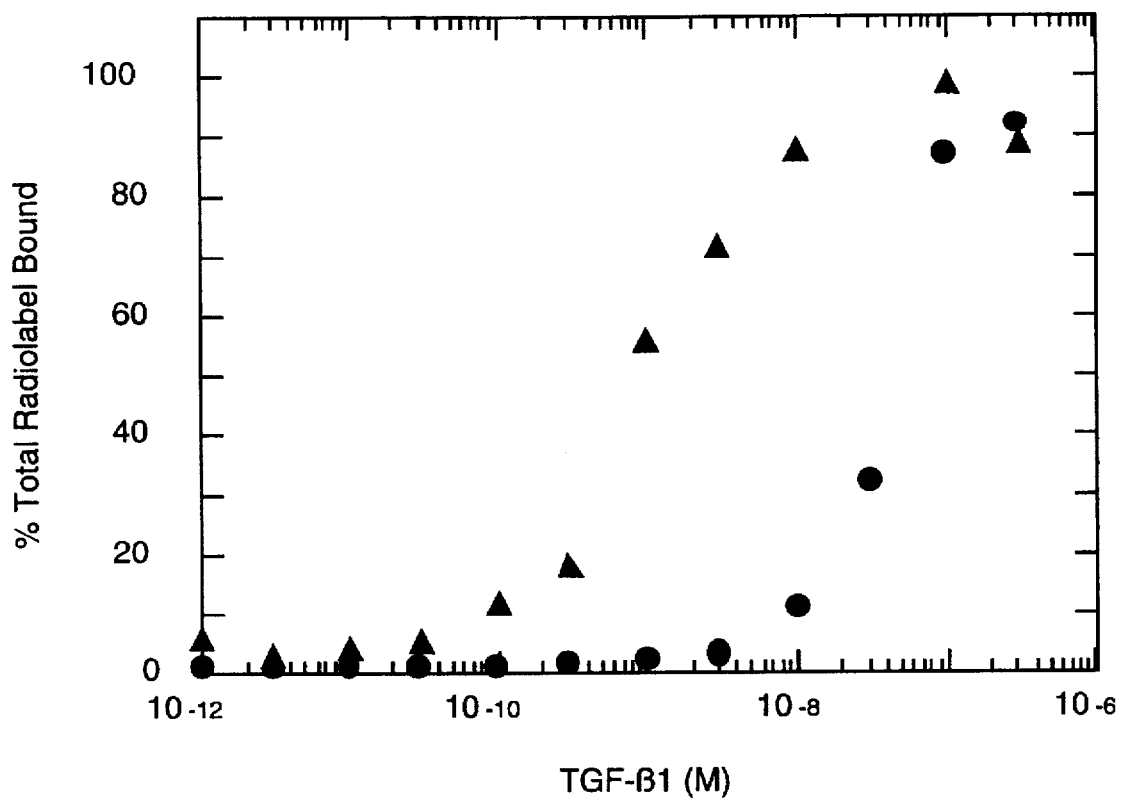
FIG. 1 shows the binding analysis of the 40D7 DNA library for TGFβ1. Binding data obtained from Round 19 (triangles) and Round 0 (circles) are shown.

This application describes high-affinity nucleic acid ligands to TGFβ identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931,473, filed Aug. 17, 1992, entitled Nucleic Acid Ligands, now U.S. Pat. No. 5,270,163, (see also WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning. 4) Those nucleic acids selected during partitioning as having the relatively higher affinity to the target are then amplified to create a new candidate mixture that is enriched in nucleic acids having a relatively higher affinity for the target. 5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications.

Diagnostic utilization may include both in vivo or in vitro diagnostic applications. The SELEX method generally, and the specific adaptations of the method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to TGFβ described heroin may specifically be used for identification of the TGFβ protein.

SELEX provides high affinity ligands of a target molecule. This represents a singular achievement that is unprecedented in the field of nucleic acids research. The present invention applies the SELEX procedure to the specific target of TGFβ1. In the Example section below, the experimental parameters used to isolate and identify the nucleic acid ligands to TGFβ1 are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), now U.S. Pat. No. 5,496,938, methods are described for obtaining improved nucleic acid ligands after SELEX has been performed. The '624 application, entitled Methods of Producing Nucleic Acid Ligands, is specifically incorporated herein by reference.

In the present invention, SELEX experiments were performed in order to identify RNA and DNA ligands with specific high affinity for TGF62 from degenerate libraries containing 40 or 60 random positions (40N or 60N) (Tables 1 and 5) (SEQ ID. NOS: 1-3, 43, 46, 49, 52). This invention includes the specific RNA ligands to TGFβ1 shown in Table 3 (SEQ ID NOS: 12-42), identified by the methods described in Examples 1 and 2. This invention further includes RNA ligands to TGFβ1 which inhibit TGFβ1 function, presumably by inhibiting the interaction or TGFβ1 with its receptor. This invention includes the specific ssDNA ligands to TGFβ1 shown in Table 6 (SEQ ID NOS: 55-89) identified by the methods described in Examples 5 and 6. The scope of the ligands covered by this invention extends to all nucleic acid ligands of TGFβ, modified and unmodified, identified according to the SELEX procedure. More specifically, this invention includes nucleic acid sequences that are substantially homologous to the ligands shown in Tables 3 and 6 (SEQ ID NOS: 12-42; 35-89). By substantially homologous it is meant a degree of primary sequence homology in excess of 70%, most preferably in excess of 80%. A review of the sequence homologies of the ligands of TGFβ shown in Tables 3 and 6 (SEQ ID NOS: 12-42; 55-89) shows that some sequences with little or no primary homology may have substantially the same ability to bind TGFβ. For these reasons, this invention also includes nucleic acid ligands that have substantially the same structure and ability to bind TGFβ as the nucleic acid ligands shown in Tables 3 and 6 (SEQ ID NOS: 12-42; 55-89). Substantially the same ability to bind TGFβ means that the affinity is within one or two orders of magnitude of the affinity of the ligands described herein. It is well within the skill of those of ordinary skill in the art to determine whether a given sequence—substantially homologous to those specifically described herein—has substantially the same ability to bind TGFβ.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 9, 1993, entitled High Affinity Nucleic Acid Ligands Containing Modified Nucleotides which is specifically incorporated heroin by reference. Other modifications are known to one of ordinary skill in the art. Such modifications may be made post-SELEX (modification of previously identified unmodified ligands) or by incorporation into the SELEX process.

As described above, because of their ability to selectively bind TGFβ, the nucleic acid ligands to TGFβ described herein are useful as pharmaceuticals. This invention, therefore, also includes a method for treating TGFβ-mediated pathological conditions by administration of a nucleic acid ligand capable of binding to TGFβ.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Examples 1–4 describe initial experiments to identify RNA with specific high affinity for TGFβ. Example 1 describes the various materials and experimental procedures used in Examples 2–4. Example 2 describes a representative method for identifying RNA ligands by the SELEX method which bind TGFβ1. Example 3 describes the affinities the ligands have for TGFβ1 and demonstrates that the ligands are capable of inhibiting the function of TGFβ1, presumably by inhibiting the interaction of TGFβ1 with its receptor. Example 4 describes which regions of the ligands are believed to be necessary for TGFβ1 binding and inhibition of TGFβ1 receptor binding. Example 5 describes another representative method for identifying RNA and DNA ligands by the SELEX method which bind TGFβ1. Example 6 reports on the binding analysis, bioassay, and sequences of a ssDNA SELEX library.

EXAMPLES

Example 1
EXPERIMENTAL PROCEDURES

This example provides the general procedures followed and incorporated in Examples 2–4.

A. Materials.

Human recombinant TGFβ1 used in this SELEX procedure was acquired from Genentech. Human recombinant TGFβ1 can also be purchased from R&D systems, Minneapolis, Minn., USA.

Biotinylated TGFβ1 was prepared by reacting TGFβ1 at 3.6 µM with an 11 fold molar excess of sulfo-NHS-biotin (Pierce, Rockford, Ill., USA) in 50 mM NaHCO$_3$ for 3 hr. in an ice bath. The reaction was acidified with 0.036 volumes of 10% acetic acid and applied to a 40 mg. Vydac (The Separations Group, Hesperia, Calif., USA) reverse phase column made in a siliconized pipet tip to separate unreacted biotin from biotinylated TGFβ1. The column was prewashed with 200 µl ethanol followed by 200 µl 1% acetic acid, the biotinylation reaction was applied, free biotin was washed through with 200 µl of 50 mM sodium acetate pH 5.5, followed by 200 µl of 20% acetonitrile and finally eluted with 200 µl of 60% acetonitrile. The sample was lyophilized and resuspended in 50 mM sodium acetate pH 5.0 at 40 µM and stored at 4° C. The TGFβ1 was spiked with 100,000 cpm iodinated TGFβ1 in order to follow recovery and to assess the success of the biotinylation reaction by measuring the fraction of the radioactivity that would bind to streptavidin coated agarose beads (Pierce) before and after biotinylation. An aliquot of the TGFβ1 before and after biotinylation was subjected to analytical reverse phase chromatography. The biotinylated TGFβ1 substantially ran as a single peak which was retarded with respect to the unbiotinylated TGFβ. A small amount (5%) of unreacted TGFβ1 could be detected. The efficiency of binding of the iodinated, biotinylated TGFβ1 to streptavidin (SA) agarose beads (30 µl) was 30% under the binding conditions used for SELEX partitioning.

Iodinated TGFβ1 was prepared by the lactoperoxidase method (50 mM sodium phosphate pH 7.3, 0.16% glucose) with BioRad Enzymo beads (BioRad, Richmond, Calif. USA) and the bound iodine separated from the free iodine by gel filtration on G25 Sephadex in 50 mM sodium acetate 0.01% Tween.

The mink lung cell line expressing the luciferase reporter gene under the control of PAI 1 promoter (Abe et al. (1994) Anal. Biochem. 216:276–284) was a gift from Dr. Dan Rifkin (Department of Cell Biology, New York Medical Center, N.Y. 10016). Luciferase was assayed by reagents purchased from Analytical Luminescence Laboratory, San Diego, Calif. USA.

2'-NH$_2$ modified CTP and UTP were prepared according to the method of Pieken et al. (1991. Science 253:314–317). DNA oligonucleotides were synthesized using standard procedures either at NeXstar Pharmaceuticals, Inc. (Boulder, Colo, USA) or by Operon Technologies (Alameda, Calif. USA). All other reagents and chemicals were purchased from standard commercial sources and sources have been indicated.

B. SELEX procedure

SELEX ligands that bind to TGFβ1 were derived essentially as described in U.S. Pat. No. 5,270,163 (see also Tuerk and Gold (1990) Science 249:505–510). To generate the starting pool of PCR template, PCR product from twenty separate PCR reactions each containing 16.1 pmol of unpurified, single stranded DNA (at least a total of $2 \times 10^{12}$ to $2 \times 10^{13}$ different molecules) were pooled before the first transcription. PCR conditions were 50 mM KCl, 10 mM Tris-HCL, pH 9, 0.1% Triton-X100, 1.5 mM MgCl$_2$, 0.2 mM of each dATP, dCTP, dGTP, and dTTP, 2 µM each primer and 0.075 units/µl of Taq DNA polymerase, 100 µl per reaction in a siliconized microfuge tube. All PCR cycles took advantage of hot start using Ampliwax (Perk and Elmer, Norwalk, Conn., USA). Duration of the initial PCR was 10 cycles; a PCR cycle was 94° C.-1', 52° C.-1', 72° C.-2'. An initial denaturation was 94° C. for 4' and the final extension at 72° C. for 5'. PCR reactions were combined, phenol/chloroform extracted, and isopropanol precipitated (2.0M ammonium acetate, 50% isopropanol) to remove primers.

Transcription reactions contained 200 nM DNA, 0.9 mM GTP, 0.9 mM 2'-NH$_2$-UTP, 0.9 mM 2'-NH$_2$-CTP, 0.5 mM ATP, 87 mM Tris-HCl pH 8.0, 17 mM MgCl$_2$, 4.4 mM spermidine, 22 mM DTT, 100 µg/ml acetylated BSA (Promega, Madison, Wis., USA) and 4 units/µl T7 RNA polymerase. (2'-F-UTP and 2'-F-CTP (United States Biochemical, Cleveland, Ohio, USA) were used at 3.0 mM, whereas UTP and CTP were used at 0.9 mM each). Transcription reactions were incubated overnight at 28° C. (at least 10 hours). After transcription the template was digested by addition of 2 µl RQ1 Dnase (Promega) for 15' at 28° C., and then extracted with phenol/CHCl$_3$, followed by three ethanol precipitations from ammonium acetate (3.9M ammonium acetate, 72% ethanol).

The RNA molecules were incubated with TGFβ1 bound to SA agarose beads as described below in Krebs-Ringer solution (KR) (120 mM NaCl, 4.8 mM KCl, 10 mM Na phosphate buffer pH 7.4, 1.2 mM MgSO$_4$, 2.6 mM CaCl$_2$) modified to include 20 mM Na-Hepes pH 7.5 and 0.2% Triton X100 (Pierce). This buffer is referred to as KRHT. TGFβ1-RNA complexes were separated from unbound RNA by washing the beads. Recovery of the selected 2'-NH$_2$ or F pyrimidine modified RNA from the agarose beads required guanidine thiocyanate extraction (5M GnSCN, 10 mM Tris-HCl, 0.1 mM EDTA, pH 7.0, 0.1M beta mercaptoethanol) or from Seradyne SA coated beads by 2% SDS (0.1M Tris-HCl pH 7.5, 50 mM NaCl, 1 mM Na$_2$EDTA, 2% SDS, 1.5mM DTT). Regular 2'-OH RNA was easily recovered under less harsh conditions with the same buffer used for the Seradyne beads containing only 0.2% SDS. After extraction and precipitation to purify and concentrate the RNA, the sample was reverse transcribed with a cloned MMLV RT with the RNase H sequence deleted. The reaction contained less than or equal to 16 nM RNA, 10 µM 3' primer, 50 mM Tris-HCL pH 8.3, 75 mM KCl, 5 mM MgCl$_2$, 10 mM DTT, 0.5 mM dNTP's. Prior to addition of buffer the RNA and the palmer were boiled together. After addition of buffer and salts the reaction was annealed for 10' at 28° C. before addition of 600 units of Superscript reverse transcriptase (Bethesda Research Labs, Gaithersburg, Md., USA) and synthesis at 50° C. for 1 hour.

PCR amplification of this cDNA (<1 pmol) resulted in approximately 250 pmol double-stranded DNA, of this 40 pmols was transcribed and used to initiate the next round of SELEX.

C. Partitioning Method for SELEX.

2.5 pmols biotinylated TGFβ1 were bound to 30 µl SA agarose beads (Pierce) in 200 µl KRHT. The mixture was incubated on a rotator at 37° C. for 15 to 30 minutes. The beads were washed three times by centrifugation and resuspension in 200 µl cold KRHT to remove unbound TGFβ1, and resuspended in a final volume of 500 µl KRHT. RNA containing 2'-NH$_2$ pyrimidines was heated at 70° C. for three minutes (RNAs containing 2'-OH or 2'-F pyrimidines were heated at 95° C.) and diluted into KRHT containing TGFβ1 bound to SA beads. The final concentration of RNA is 1 µM and the TGFβ1 was 5 nM. Binding occurs with rotation at 37° C. for 30 minutes. Beads were washed by centrifugation and resuspension three times with 200 µl binding buffer to remove unbound RNA. RNA was eluted from the beads as described above.

D. Binding assays

Two binding assays for ligands to TGFβ1 gave equivalent results wherever tested. In the SA bead assay the biotinylated TGFβ1 was serially diluted in KRHT in polypropylene tubes (Linbro, ICN, Irvine, Calif., USA) and bound to the beads as described above. After unbound TGFβ1 was washed away, trace quantities of $^{32}$P -labeled RNA(<0.1 nM) were added to each tube and vortexed to mix. After static incubation at 37° C. for 30 minutes, the unbound RNA was removed by washing three times with 200 µl of KRHT.

In the nitrocellulose filter binding assay, TGFβ1 was serially diluted in KRH containing 0.1% defatted BSA (Fluka radioimmunoassay grade, Fluka, Hauppauge, N.Y., USA) as carrier instead of Triton X-100. Incubation with RNA tracer was as above. Samples were pipetted with a multiwell pipettor onto a multiwell manifold holding a sheet of wet BioRad 0.45 micron nitrocellulose, aspirated, and washed three times with 200 µl KRH (containing no BSA). The filters were air dried and counted in a liquid scintillation counter (Beckmann Instruments, Palo Alto, Calif.)

The equation used to fit the binding of ligands to TGFβ1 describes the binding of a ligand to a receptor (in this case TGFβ1) that follows the laws of mass action and for which there is a single binding site: $Y = B_{max} \cdot X / (Kd+X)$: where Y is the fraction of the ligand bound, $B_{max}$ is the maximum fraction of the ligand bound, X is the concentration of TGFβ1 and Kd is the dissociation constant of TGFβ1 and the ligand. Data points were fit by nonlinear regression using the computer program Graphpad Prism (Graphpad Software, San Diego, Calif.). The algorithm minimized the sum of the squares of the actual distance of the points from the curve. Convergence was reached when two consecutive iterations changed the sum-of-squares by less than 0.01%.

E. Cloning and Sequencing

SELEX experiments are described in Table 2. Primers for SELEX experiments 1 and 2 shown in Table 1 contain recognition sites for the restriction endonucleases SacI (5' primer T7SacBam; SEQ ID NO: 7) and XbaI (3' primer 3XH; SEQ ID NO:9). PCR products from SELEX experiments 1 and 2 were cloned directionally into SacI/XbaI digested pGem 9zf (Promega). 5' primer T7SB2N (SEQ ID NO: 8) and 3' primer 3XH (SEQ ID NO: 9) (Table 1) were used for SELEX experiments 3–9. PCR products from SELEX experiments 3–9 were cloned directionally into the BamH1/XbaI site of a modified pGem9zf :BamH1 cloning vector. The BamH1 site was engineered into pGem9zf in the following way. A clone isolated from library 2 (lib2-6-2) that did not bind to TGFβ1 (sequence not shown) was digested with BaMH1 and XbaI. The sequence flanking the cloning site of the modified pGem9zf vector is shown in Table 1 (SEQ ID NOS: 10–11).

After digestion of the plasmid with restriction endonuclease and dephosphorylation with CIP (calf intestinal phosphatase), vectors were gel purified. Inserts were ligated and recombinant plasmids were transformed into E. coli strain DH10B (Bethesda Research Labs). Plasmid DNA was prepared by alkaline lysis, mini prep procedure. Twenty-two clones representing 9 unique sequences were sequenced at random from libraries 1 and 2. 50 clones were sequenced from libraries 3–9 using a single dideoxy G reaction (called G track). The sequencing ladders were compared and organized for similarities. Selected clones from each family were chosen for complete sequence analysis. TGFβ1 binding assays were performed on transcripts representing different G sequences in each library. Out of a total of 140 binding assays, 27 ligands bound with a Kd less than 10 nM, and 21 of these were sequenced. Clones were sequenced with the Sequenase sequencing kit (United States Biochemical Corporation, Cleveland, Ohio).

F. Ligand Truncation

Truncation experiments were carded out to determine the minimal sequence necessary for high affinity binding of the RNA ligands to TGFβ1. For 3' boundary determination, RNA ligands were 5' end-labeled with γ-$^{32}$P-ATP using T4 polynucleotide kinase. 5' boundaries were established with 3' end-labeled ligands using α-$^{32}$P-pCp and T4 RNA ligase. After partial alkaline hydrolysis, radiolabeled RNA ligands were incubated with TGFβ1 at concentrations ranging from 1 nM to 50 nM and protein-bound RNA was separated by nitrocellulose partitioning. RNA truncates were analyzed on a high-resolution denaturing polyacrylamide gel. A ladder of radioactively labeled ligands terminating with G-residues was generated by partial RNase T1 digestion and was used as markers.

G. Inhibition of TGFβ1 function

TGFβ1 signal transduction begins with binding to a cell surface receptor and results in the induction of transcription of a variety of genes. One of these genes is Pai1. The TGFβ1 assay utilizes the mink lung epithelial cell (MLEC) carrying the luciferase reporter gene fused to the Pai 1 promoter. The MLEC has TGFβ1 receptors on its cell surface. Thus one can measure the response of the cells to TGFβ1 and the effective concentration of TGFβ1 in the culture media by measuring the luciferase enzyme activity after a period of induction.

Mink lung epithelial cells (MLEC) carrying the Pai1/luc construct were maintained in DME containing 10% fetal bovine serum and 400 µg/ml G418. MLEC-Pai1/luc cells were plated at 3.2×10$^4$ cells per well in a 96 well Falcon plate, in 100 µl of DME+10% fetal bovine serum overnight. Media was made from autoclaved water. The cells were washed three times (100 µl) in serum free DME plus Solution A (1:1). Solution A is 30 mM Hepes pH 7.6, 10 mM glucose, 3.0 mM KCl, 131 mM NaCl, 1.0 mM disodium phosphate. Samples (100 μl) were added in DME containing 20 mM Hepes pH 7.5, and 0.1% BSA (Fluka, radioimmunoassay grade). All samples were in triplicate. After six hours at 37° C. in a 5% $CO_2$ incubator the media was removed and cells were washed three times (100 μl each) in cold PBS. Lysis buffer (75 μl) (Analytical Luminescence Laboratory) was added and the plates incubated on ice for 20'. The plates were sealed and frozen at −80° C. until assayed. Samples (25 μl) were assayed for luciferase activity with the Enhanced Luciferase Assay Kit from Analytical Luminescence Laboratory (San Diego, Calif., USA) according to the manufacturers instructions using the Berthold Microlumat LB96P luminometer. Luminescence is reproducibly a function of TGFβ1 concentration added to the media.

Ligands tested for inhibition of TGFβ1 activity were tested at a minimum of five concentrations. The ligands were serially diluted in DME, 20 mM Hepes pH 7.5, 0.1% Fluka BSA in polypropylene tubes and an equal volume of media containing 12 pM TGFβ1 was added to each tube, vortexed and transferred to the cells without further incubation. From the TGFβ1 standard curve included on every plate the effective concentration of TGFβ1 in the presence of the inhibitory ligands was determined by the reduction in luminescence measured. Some ligands were tested at both 3 pM and 6 pM TGFβ1 with the same results. To determine the $IC_{50}$ (the concentration of SELEX ligand necessary to reduce the TGFβ1 activity 50%), the five values obtained for each ligand were plotted and the value at 50% inhibition was determined graphically using Graphpad Prism assuming a hyperbolic fit of the data and using non-linear regression.

Example 2
RNA LIGANDS TO TGFβ1
A. SELEX experiments

In order to generate RNA ligands to TGFβ1, nine SELEX experiments, as summarized in Table 2, were performed using the methods described in Example 1. As shown in Table 1, the RNA pools differ in the number of random bases present in the central portion of the molecules: 40 nucleotides in the 40N6 (SEQ ID NO: 2) SELEX and 64 nucleotides in the 64N6 and lib2-6-1RN6 (SEQ ID NOS: 1, 3) SELEX experiment. Since the goal was to select RNA ligands that not only bound to TGFβ1 but also blocked receptor binding, the large random region (64N) was chosen. In two experiments, a shorter random region (40N) was also included. Ligands to TGFβ1 were very rare with 40N and were qualitatively the same as the 64N6 ligands selected.

The sequences of clones from the SELEX experiments are shown in Table 3 (SEQ ID NOS: 12–42). The pyrimidines used in the various SELEX experiments differed at the 2' position of the sugar (Table 2). In the first two SELEX experiments, ligands were evolved as 2'-OH pyrimidines. Ligands were post-SELEX modified with 2'-$NH_2$ or 2'-F-substituted pyrimidines to see if they retained TGFβ1 binding. Since the 2' substitutions rendered the ligands resistant to RNase A they were also tested in the cell culture assay for inhibition of TGFβ1 activity. One such ligand lib2-6-1 (Group D, Table 3) (SEQ ID NO: 35) when substituted with 2-$NH_2$-UTP and 2'-F-CTP was shown to inhibit TGFβ1 receptor mediated activity. To select more ligands, six more independent SELEX experiments (lib3-7 and lib9) were performed using the 2'-F and 2'-$NH_2$ -substituted pyrimidines during the evolution process. In experiment lib8 the biologically active clone lib2-6-1 (SEQ ID NO: 35) was randomized and subjected to re-selection to see if the binding and inhibition behavior of the clone could be improved. Lib8 was evolved as a 2'-OH pyrimidine RNA. In some cases, post-SELEX modification of TGFβ1 ligands derived from experiments 3–9 were performed, eg. to determine if a ligand evolved with 2'-F pyrimidine substitutions would also bind with 2'-$NH_2$ substitutions.

Each starting pool for a SELEX experiment contained $3 \times 10^{14}$ RNA molecules (500 pmol). The affinity of the starting RNA for TGFβ1 was estimated to be greater than 50 mM. After 4 rounds of SELEX, the affinities of the evolving pools had improved to approximately 10 nM and did not shift significantly in subsequent rounds. RNA was bulk sequenced and found to be non-random and cloned.

Lib1 took 20 rounds to evolve since optimum concentrations of TGFβ1 were not used until round 15 and libraries 5, 6 and 7 took longer to evolve because optimum conditions for recovery of bound ligands during the partitioning step in SELEX were not introduced until round 8. Optimum TGFβ1 concentrations and partitioning conditions are described in Example 1.

B. RNA Sequences

Many clones in a SELEX library are identical or similar in sequence. The libraries were screened by G track and only representatives of each G track type were tested in a binding assay. The binding assay was five points (16.5 nM, 5.5 nM, 1.8 nM, 0.6 nM, and 0.2 nM) and could detect only those SELEX clones with a Kd less than or equal to 10 nM. RNA ligands that bound well (Kd<10 nM) in the binding assay were sequenced. The sequences were inspected by eye and analyzed using computer programs which perform alignments and fold nucleic acid sequences to predict regions of secondary structure. Ligands were classified into five groups (A, B, C, D, and orphans) by sequence homology. Each group has characteristic allowable 2' substitutions.

58 clones were identified by G track from 7 separate SELEX experiments to belong to group A ligands (Table 3) (SEQ ID NOS: 12–42). 15 clones were sequenced; 13 were similar but not identical, whereas 3 clones, lib3-13 (SEQ ID NO: 12), lib5-6 and lib5-13, were identical. Group A ligands were recovered from seven of the eight SELEX libraries which included libraries evolved as 2'-$NH_2$, 2'-OH or 2'-F-substituted pyrimidines as well as a library evolved as 2'-F-UTP, 2'-$NH_2$-CTP. Post SELEX modification indicates that 2'-$NH_2$-UTP, 2'-F-CTP does not disrupt binding of lib8-9 to TGFβ1, thus the structure of Group A ligands appears to not require a specific 2' moiety on the pyrimidine sugar in order to maintain binding.

Group B ligands bind both as 2'-$NH_2$ and 2'-F pyrimidine substituted RNA. 28 Group B clones were detected by G track analysis from 3 libraries. Two of the libraries were evolved as 2'-$NH_2$ and one as 2'-F library. Four clones were sequenced, two were identical (lib5-47 and lib4-12)(SEQ ID NO: 28). An internal deletion can occur in group B, as does in lib 3-44 (SEQ ID NO: 29). The 40N orphan, lib3-42 was placed in Group B on the basis of secondary structure. The internal deletion in lib3-44, the binding affinity, the bioactivity and boundary experiments all support the placement of lib3-42 in this group.

Group C ligands bind as 2'-OH or 2'-F ligands as expected, since members of this group were evolved as 2'-OH ligands in lib 1 and as 2'-F pyrimidine substituted ligands in lib 6. Lib 1-20-3 was post SELEX modified and as 2'-F derivative. Lib 1-20-3 (SEQ ID NO: 32) did not bind with 2'-$NH_2$ pyrimidines incorporated.

Group D ligand, lib2-6-1 (SEQ ID NO: 35) was isolated after 2'-OH SELEX but was post SELEX modified and binds well as a 2'-$NH_2$-UTP and 2'-F-CTP pyrimidine derivative. Lib2-6-1 does not bind well to TGFβ1 with 2'-$NH_2$, 2'-F or 2'F-UTP, 2'-$NH_2$-CTP -substituted pyrimidines. Variants of Group D were only reselected in two other SELEX experiments, lib8, a 2'-OH library, and lib 9, a 2'-NH$_2$-UTP, 2'-F CTP library, supporting the observation that there is specificity for the 2' pyrimidine position in this ligand.

The group labeled orphans are not homologous to each other and no variant sequences for these ligands have been determined. G track indicates that eight 40N clones similar to lib3-45 (SEQ ID NO: 39) were isolated from two libraries. Two of the eight were sequenced and are identical. Lib3-45 binds whether it contains 2'-NH$_2$ or 2'-F substituted pyrimidines or the 2'-F-UTP, 2'-NH$_2$-CTP combination. Lib1-20-5 (SEQ ID NO: 40) isolated as a 2'-OH ligand binds as a 2'-F, whereas lib1-20-12 (SEQ ID NO: 41) and lib2-6-8 (SEQ ID NO: 42) bind well only as 2'-OH pyrimidines and will not tolerate 2'-NH$_2$ or 2'-F post SELEX modifications.

As it was unusual that similar sequences were obtained from different selex experiments containing different modifications, another set of selex experiments was performed in search of RNA and ssDNA ligands to TGFβ1 as described in examples 5 and 6 infra.

Example 3
INHIBITION OF TGFβ1 RECEPTOR BINDING

The Kds and B$_{max}$ values reported in Table 4 for Group A ligands are for the 2'-NH$_2$ substituted version of the ligand unless otherwise noted. B$_{max}$ for the Group A ligands was 0.38±0.12 (n=14) which is in agreement with the measured retention of TGFβ1 on the nitrocellulose filters. The Kd's for Group A ligands were all similar, 2.2±1.1 nM (n=14). Where measured nitrocellulose and SA agarose bead binding assays gave equivalent results.

The IC$_{50}$'s in Table 4 for Group A ligands were all tested with the 2'-NH$_2$ pyrimidine substituted ligands except where indicated. 2'-NH$_2$ ligands were used in the tissue culture bio-assay since they exhibited the greatest stability under the conditions of the bio-assay. Five out of ten Group A ligands tested inhibited TGFβ1 receptor activity. IC$_{50}$ values for the inhibitors were typically 25 fold above the Kd for TGFβ1. The data are reproducible; the Kd for ligand lib3-13 was 0.83±0.11 nM (n=3) and the IC$_{50}$ for lib3-13 was 25±14 nM (n=4). RNA concentrations in the bioassays are all estimates based on an assumed extinction coefficient and 100% purity of the ligand. The RNA concentrations may, therefore, be overestimated during the bio-assay which in turn would overestimate the IC$_{50}$.

Another five Group A ligands did not inhibit TGFβ receptor binding activity. One obvious difference between the non-bioactive ligands, lib2-6-4 (SEQ ID NO:20), lib5-48 (SEQ ID NO: 19), and lib6-23(SEQ ID NO:21), and the bioactive ligands is the substitution at nucleotide 72. Lib7-21 (SEQ ID NO: 23) and lib7-43 (SEQ ID NO: 24) were tested as 2'-F-UTP, 2'-NH$_2$-CTP ligands for bio-activity. These ligands were not bioactive despite their high affinity to TGFβ. In conclusion, binding and bioactivity are separable functions of the TGFβ Group A ligands.

Group B ligands have different binding properties than Group A ligands (Table 4). Both the Kd (0.63±0.5 nM, n=4) and B$_{max}$ (0.14±0.04, n=4) are lower for Group B ligands. One Group B inhibitor, lib4-12 (SEQ ID No: 28), actually appears to stimulate TGFβ1 activity in the tissue culture bio-assay at low concentrations. The basis of this mixed agonist/antagonist behavior has not been determined. The best inhibitor in this group, lib3-42 (SEQ ID NO: 30) has an IC$_{50}$ of 22 nM and had no agonist behavior over the concentration ranges tested.

Group C ligands were tested as 2'-F derivatives and were not bio-active. Neither was the 2'-F orphans lib1-20-5 (SEQ ID NO: 40). The 2'-NH$_2$, 40N orphan, lib3-45 (SEQ ID NO: 39) is an example of another ligand with high affinity for TGFβ1 and no ability to inhibit TGFβ1 receptor binding.

Group D ligands were tested in the bio-assay as 2'-NH$_2$-UTP, 2'-F-CTP derivatives. Both lib2-6-1 (SEQ ID NO: 35) and the truncated version lib2-6-1-81 (SEQ ID NO: 36) can inhibit TGFβ1 receptor binding; however, a single mutation from a C to a G at position 53 decreases bio-activity in clone lib8-23 (SEQ ID NO: 37). Similarly a 2 base pair deletion in clone lib6-30 (SEQ ID NO: 34) at positions corresponding to nucleotides 67 and 68 in lib2-6-1 (SEQ ID NO: 35) increases binding by 10 fold but eliminates bio-activity.

Lib2-6-1 (SEQ ID NO: 35) was shown to be fully effective only against TGFβ1 and not TGFβ2 and TGFβ3. Lib2-6-1 was biologically active in the presence of 10% horse serum in the cell culture medium in addition to the 0.1% BSA. Thus the ligand demonstrates specificity towards TGFβ1 which is not interferred with by the presence of the horse serum in this assay. The biggest indication that the inhibition of TGFβ1 receptor binding is a specific phenomenon is the fact that not all TGFβ1 ligands block receptor binding, but the ones that do, do so reproducibly. There are no examples of ligands that do not bind to TGFβ1 blocking TGFβ1 receptor binding activity.

In summary, RNA ligands that can block TGFβ1 receptor binding are a subset of ligands. Binding is necessary but not sufficient for bio-activity. Roughly 50% of the high affinity ligands tested were inhibitors. Of the inhibitors, 30% were good inhibitors (IC$_{50}$ <25 nM).

Example 4
BOUNDARY ANALYSIS

Truncation experiments were done on a number of TGFβ1ligands to determine the nucleotides essential for binding. Group A ligands, lib3-13 (SEQ ID NO: 12) and lib8-9 (SEQ ID NO: 16), were truncated with consistent results. The fragment lib3-13-79 binds to TGFβ1, thus none of the nucleotides 3' to nucleotide 79 in lib3-13 am essential for binding. Similarly when all nucleotides 5' to nucleotide 38 are deleted the remaining fragment, lib3-13-(38-123) can still bind to TGFβ1. The 5' boundary is in agreement with the sequence lib6-23 (SEQ ID NO: 21), which has a deletion corresponding to nucleotides 19-36 of lib3-13 (SEQ ID NO: 25), and still binds to TGFβ1. Thus, all high affinity binding determinants for Group A clones may lie wholly within the random region and may correspond to a 42 nucleotide fragment, lib3-13-(38-79). Many Group A ligands contain deletions or substitutions within the predicted essential binding domain, in the region corresponding to lib3-13-(72-81). The deletion and substitution in lib4-32 have no effect on its 3' boundary which corresponds to lib3-13 nucleotide 80. Thus, the 3' boundary is probably correct and the alterations in nucleotide sequence 72-81 are ones that do not significantly alter the nucleic acid structure required for binding. Mutations in this region, most notably nucleotide 72 may, however, modify the ability of the ligand to block TGFβ1 receptor binding as noted earlier.

Boundary analysis of the 3' end of Group B ligand, lib4-12 (SEQ ID NO: 28), predicts that nothing beyond nucleotide 72 is required for TGFβ1 binding. When the 5' boundary of lib4-12 was determined, all but the first three nucleotides were required for binding, indicating that the 5' constant region is an essential part of the ligand at least when the boundary of the full length ligand was determined. Assuming that ligand lib3-44 (SEQ ID NO: 29) has a similar binding determinant as lib4-12 (SEQ ID NO: 28), we can also conclude that nucleotides 37-46 of lib4-12 are not required for binding since these are deleted in lib3-44 and lib3-42 (SEQ ID NO: 30).

The 3' constant region is not necessary for binding in Group C and D ligands. Both ligand types bind without the 3' nucleotides in the constant region. Lib1-20-3-82, an 82 nucleotide truncated version of lib1-20-3, binds as well as the full length lib1-20-3. Likewise binding and bioactivity of lib2-6-1 (SEQ ID NO: 35) is unaffected by the 3' truncation found in lib2-6-1-81 (SEQ ID NO: 36).

Example 5
EXPERIMENTAL PROCEDURES

In the preferred embodiment, a second set of SELEX experiments was performed in search of RNA and DNA ligands with specific high affinity for TGFβ1 from degenerate libraries containing 40 random positions (40N). This Example provides the general procedures followed and incorporated in Example 6.

A. Materials

M-MLV superscript reverse transcriptase was purchased from Gibco BRL (Gaithersburg, Md.). T7 RNA polymerase was purified according to standard procedures at NeXstar Pharmaceuticals, Inc. (Boulder, Colo.). Taq DNA polymerase (Amplitaq) was from Perkin Elmer/Cetus (Richmond, Calif.). T4 polynucleotide kinase, DNA polymerase (Klenow fragment), and alkaline phosphatase were purchased from New England Biolabs, Inc. (Beverly, Mass.). The 2'-amino substituted nucleotide triphosphates amino-UTP and amino-CTP were synthesized according to standard procedures at NeXstar Pharmaceuticals, Inc. (Boulder, Colo.). Other reagents used in this work were of the highest quality obtainable.

B. Nucleic Acids

RNAs were synthesized by in vitro transcription using double-stranded DNA oligonucleotides and T7 RNA polymerase. DNA oligonucleotides (Table 5) were purchased from Operon, Inc. (Alameda, Calif.) and purified by 6% preparative polyacrylamide gel electrophoresis. PCR amplification was performed in 50 mM KCl, 10 mM Tris-HCl (pH 8.6), 2.5 mM $MgCl_2$, 170 mg/mL BSA, and dNTPs (present at 1 mM each). Taq DNA polymerase was used at 100 units per 0.1 mL reaction, and the 5'- and 3'-primers were present at 1 mM. Transcription was performed in 40 mM NaCl, 10 mM dithiothreitol, 50 mM Tris-acetate (pH 8.0), 8 mM magnesium acetate, 2 mM spermidine, and 2 mM NTP. T7 RNA polymerase was present at 1 unit/mL. The reaction was incubated at 28 degrees for 16 hours and then treated with 20 units of DNAse I for an additional 10 min at 37 degrees. The reaction was stopped by the addition of one half volume of loading buffer (93% formamide, 10 mM EDTA, pH 8.0) and heated to 95 degrees for 3 min prior to electrophoresis on a 6% polyacrylamide/8M urea denaturing gel. The RNA transcript was visualized by UV shadowing and was excised from the gel and eluted into TE buffer (10 mM Tris-acetate pH 8.0, 2 mM EDTA). The RNA transcript was ethanol precipitated, dried under vacuum, and redissolved in distilled $H_2O$. The concentration of RNA as well as single-stranded DNA was quantified by measuring the $A_{260}$ and assuming that 1 $A_{260}$ unit equaled 40 mg/mL and 33 mg/mL, respectively.

C. Evolution of High-Affinity Ligands

SELEX ligands that bind to TGFβ1 were derived essentially as described in U.S. Pat. No. 5,270,163 (see also Tuerk and Gold (1990) Science 249:505–510) using the oligonucleotides illustrated in Table 5 (SEQ ID NOS: 43–54). The DNA templates contained a 40-nucleotide (40N) variable sequence generated by mixed-nucleotide DNA synthesis, as well as 5'- and 3'-fixed sequences, necessary for PCR amplification of the template. The 5'-fixed sequence of oligonucleotides 40N7 and 40N8 also contained a T7 RNA polymerase promoter. RNA for the first round of RNA SELEX was transcribed from double-stranded DNA templates generated by primer extension on single-stranded DNA templates 40N7 and 40N8 with the Klenow fragment of DNA polymerase I. RNA SELEX consisted of up to 15 rounds of RNA synthesis, binding to target, partitioning of bound and unbound RNA by nitrocellulose filtration, cDNA synthesis, and PCR amplification to regenerate the double-stranded DNA template. Binding to the target by the RNA pool was performed in binding buffer A (120 mM NaCl, 2.5 mM KCl, 0.12 mM $MgSO_4$, 40 mM HEPES, 20 mM $NaH_2PO_4/Na_2HPO_4$ pH 7.4, 0.01% HSA) at 37 degrees for at least 10 min prior to filtration. In contrast, the first round of single-stranded DNA SELEX was performed by using the synthetically synthesized oligonucleotides 40D7 and 40D8 directly. SELEX consisted of 25 rounds of binding to target, partitioning of bound and unbound single-stranded DNA by nitrocellulose filtration, PCR amplification to generate a double-stranded DNA population, and preparative polyacrylamide gel electrophoresis to purify single-stranded DNA for the next round of SELEX. Binding of the target to the single-stranded DNA pool was performed in binding buffer B (150 mM NaCl, 10 mM Tris-acetate pH 7.5, 0.001% BSA) at 37 degrees for at least 15 rain prior to filtration. Radiolabeling of RNA as well as DNA repertoires was performed by incubation of 5 picomoles nucleic acid, 2 units of T4 polynucleotide kinase, and 6 mL [$\gamma^{32}P$]ATP (800 Ci/mmol) in a volume of 10 mL at 37 degrees for 30 min. The concentration of nucleic acid at each round of the SELEX experiment varied between 1500 nM and 1 nM while the concentration of the target TGFβ1 varied between 150 nM and 0.03 nM.

D. Cloning and Sequencing of Ligands

Cloning of the nucleic acid repertoire was performed as described by Tuerk and Gold (1990) Science 249:505–510 using double-stranded DNA that was generated from the RNA repertoire by PCR amplification. PCR-amplified DNA was digested with the restriction enzymes SphI and HindIII and ligated into compatible sites within pGEM. Ligated plasmids were transformed into E. coli and plated onto LB agar containing 5-bromo-4-chloro-3indolyl β-D-galactoside, isopropyl thiogalactoside, and 100 mg/mL ampicillin. Colonies not expressing β-galactosidase were analyzed. Sequencing of DNA was performed as described by Tuerk and Gold (1990) using the dideoxynucleotide procedure of Sanger et al. (1977) Proc. Natl. Acad. Sci. USA 74:5463–5467. Plasmids were isolated from E. coli by the alkaline lysis miniprep procedure (Manitatis et al. (1982) in Molecular Cloning: A laboratory Manual, Cold Spring Harbor Laboratory Press, Cold Spring Harbor, N.Y.). DNA was incubated in 50 mM Tris-HCl (pH 8.3), 60 mM NaCl, 6 mM magnesium acetate, and 1 mM DTT with 0.4 mM dNTP and 0.2 mM dideoxy-NTP for 20 min at 48 degrees. DNA polymerase was present at 4 units per reaction. The reactions were stopped by the addition of 10 mL of loading buffer and heated to 95 degrees for 3 min prior to gel electrophoresis on a 6% polyacrylamine/8M urea denaturing gel. G-track sequencing was performed as described and provided a convenient method to quickly screen the cloned library for ligands of different sequence. Briefly, the G-track sequencing reaction contained 50 mM Tris-HCl (pH 8.3), 60 mM NaCl, 6 mM magnesium acetate, and 1 mM DTT with 0.4 mM dNTP, 0.2 mM dideoxy-GTP, and 4 units of DNA polymerase. The reaction was performed at 48 degrees for 20 rain and was stopped by the addition of 10 uL of loading buffer and heated to 95 degrees for 3 min prior to gel electrophoresis on a 6% polyacrylamide/8M urea denaturing gel.

Example 6
BINDING ANALYSIS, BIOASSAY RESULTS, AND SEQUENCES OF A ssDNA LIBRARY Binding analysis of the 40D7 DNA library for TGF-B1 is shown in FIG. 1. Binding data obtained from round 19 (triangles) and round 0 (circles) are shown. The experiment was performed by incubating nucleic acid (less than 1 nM) and the indicated concentration of TGF-β1 in Binding Buffer (150 mM NaCl, 10 mM Tris-acetate pH 8.2, 0.001% BSA) for 15 minutes at 37 degrees in a volume of 0.1 mL. Samples were filtered through nitrecellulose and were immediately followed by 3 mL of TE Buffer (10 mM Tris-acetate pH 8.0, 0.1 mM EDTA). The percentage of radiolabel bound was calculated from the amount of radiolabel retained on the nitrecellulose falter and the total radiolabel added to the binding reaction. The results show that the apparent Kd of the 40D7 library is 1 nM, whereas the starting pool has an apparent Kd of 30 nM. Thus, the 40D7 library shows an increase of about three fold in binding.

Figure 2:
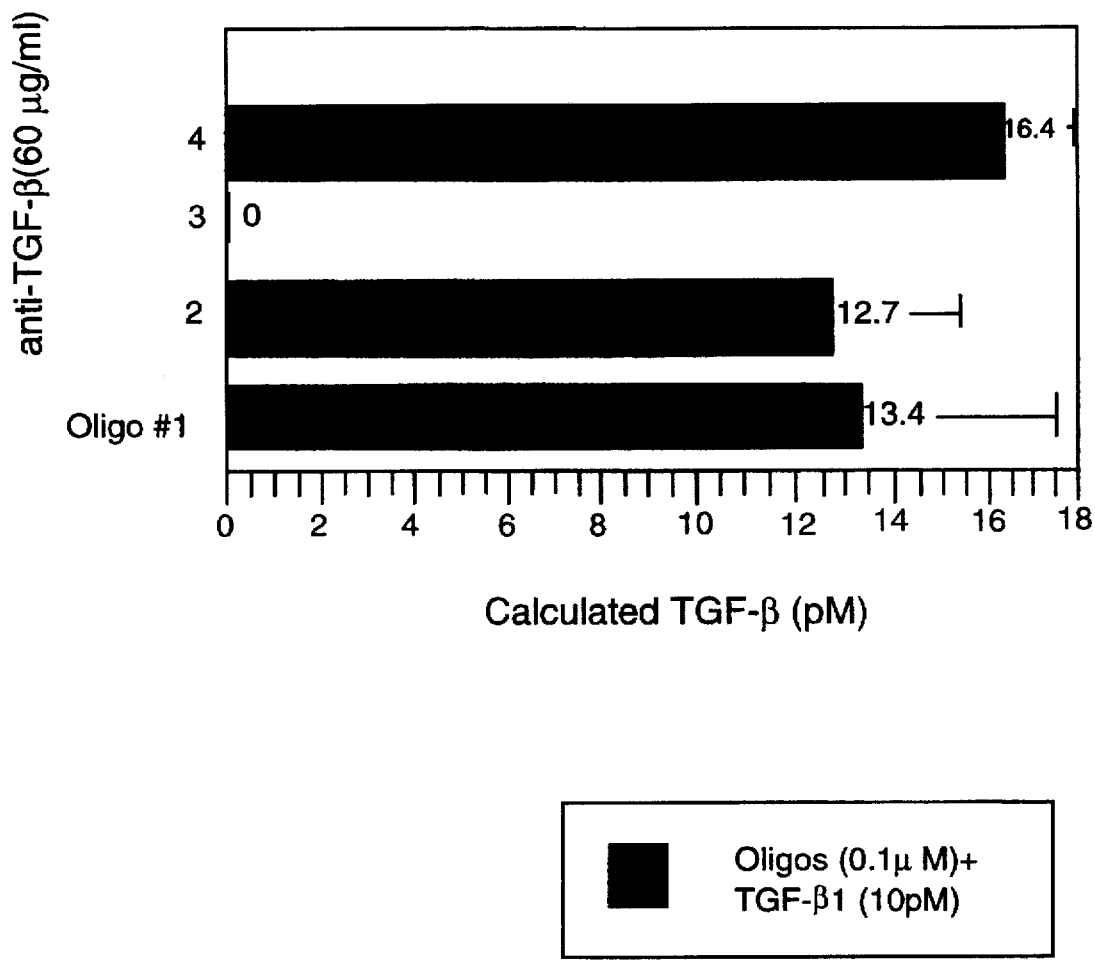
FIG. 2 shows the results of the PAI-luciferase assay of TGFβ1 (10 pM) incubated with oligonucleotides (0.1 μM) or anti-TGFβ (60 μg/ml).

A PAI-luciferase assay to detect TGFβ-1 activity in the presence of the nucleic acid libraries generated in Example 5 was performed as described in Abe et al. (1994) Analytical Biochem. 216:276–284. Mink lung epithelial cells containing the PAI-luciferase reporter gene were incubated with TGF-β1 (10 pM) and oligonucleotides from the DNA libraries or anti -TGF-B antibody (60 µg/mL). The mink lung epithelial cells were incubated for 18 hours and oligonucleotides were pre-incubated with TGF-β1 before the assay and re-added after 8 hours. Addition of oligonucleotides alone (100 nM) to the cell culture did not affect the assay (data not shown). The identity of the oligonucleotide libraries as well as their effect on luciferase activity is indicated in FIG. 2. The ssDNA library 40N7 completely inhibited the activity of TGF-B1, while the control (an equal concentration of randomized nucleic acid) showed a small stimulation of TGF-B1 activity.

Based on the results of the binding analysis and PAI-luciferase assay, DNA ligands from the 40N7 library were sequenced as described in Example 5. The sequences are shown in Table 6 (SEQ ID NO: 55–89). As the DNA 40N7 library showed inhibition in the PAI-luciferase bioassay, it is reasonable to suggest that the individual clones from the library are TGFβ1 binders.

TABLE 1

Nucleic Acid Sequences Used in SELEX Experiments described in Examples 1–4

| | SEQ. ID NO. |
|---|---|
| Starting RNAs: <br> 5' GGGGGAGAACGCGGAUCC[-64N] AAGCUUCGCUCUAGAUCUCCCUUUAGU GAGGGUUA 3' | 1 |
| 40N6 transcript: <br> 5' GGGGGAGAACGCGGAUCC [-40N-] AAGCUUCGCUCUAGAUCUCCCUUUAGU GAGGGUUA 3' | 2 |
| randomized lib2-6-1 transcript*: <br> 5' GGGGGAGAACGCGGAUCC[ugucuccaccgccgauacuggggguuccuggggccccuccauggagg aggggggugguucggaga]AAGCUUCGCUCUAGAUCUCCCUUUAGUGAGGGUUA 3' | 3 |
| Starting DNA templates: <br> Z-54 (64N60): <br> 5'GGGAGAACGCGGATCC [-64N-] AAGCTTCGCTCTAGA3' | 4 |
| Z-55 (40N6): <br> 5'GGGAGAACGCGGATCC [-40N-] AAGCTTCGCTCTAGA3' | 5 |
| D-123(randomized lib2-6-1)*: <br> 5'GGGGGAGAACGCGGATCC[tgtctccaccgccgatactggggttcctggggcccctccatggaggagggggg tggttcggaga]AAGCTTCGCTCTAG 3' | 6 |
| PCR and cloning primers: <br> T7SacBam: <br> 5'TAATACGACTCACTATAGGGGGAGTCTGCGGATCC3' <br>                                              SacI       BamH1 | 7 |
| T7SB2N: <br> 5'TAATACGACTCACTATAGGGGGAGAACGCGGATCC3' <br>                                                     BamH1 | 8 |
| 3XH: <br> 5'TAACCCTCACTAAAGGGAGATCTAGAGCGAAGCTT3' <br>                                         XbaI       HindIII | 9 |
| BamH1 cloning site engineered into pGem9zf to clone SELEX experiments 3–9. | |
| GATTTAGGTGACACTATAGAATATGCATCACTAGTAAGCTTTGCTCTAGA <br> SP6 promoter                                                 XbaI | 10 |
| GGATCCCGGAGCTCCCTATAGTGAGTCGTATTA <br> BamH1                   T7 promoter | 11 |

*GAUC or GATC, these bases only gauc or gact 62.5% specified base, 12.5% the other three bases

TABLE 2

RNA SELEX Experiments described in Examples 1–4: template, pyrimidine nucleotides, and round cloned.

| SELEX exp | template* | 2'substituted UTP | 2'substituted CTP | Round cloned |
|---|---|---|---|---|
| lib1 | 64N6 | OH | OH | 20 |
| lib2 | 64N6 | OH | OH | 6 |
| lib3 | 40N6 + 64N6 | F | F | 4 |
| lib4 | 40N6 + 64N6 | NH$_2$ | NH$_2$ | 5 |
| lib5 | 64N6 | NH$_2$ | NH$_2$ | 13 |
| lib6 | 64N6 | F | F | 13 |
| lib7 | 64N6 | F | NH$_2$ | 14 |
| lib8 | D-123 | OH | OH | 6 |
| lib9 | 64N6 | NH$_2$ | F | 5 |

*Sequences of templates are described in Table 1.

TABLE 3

TGFβ Binding ligands

| clone | 5' CONSTANT | VARIABLE | 3' CONSTANT | SEQ ID NO. |
|---|---|---|---|---|
| Group A | | | | |
| lib3 13 | gggggagaaacgcggauuc | GAGCAAUCCCAGGCGCAUAGCUUCCGAGUAGACAGGAGGGGUUGGAUGUGGCGUCUACUCGGUGUCGUG | aagcuucgcucuagaucucccuuuagugaggguua | 12 |
| 3 | gggggagaaacgcggauuc | GAGCAAUCCCAGGCGCAUAGCUUCCGAGUAGACAGGAGGAGGGGUUGGAUGUGGCGUCUACUCGGUGUCGUG | aagcuucgcucuagaucucccuuuagugaggguua | 13 |
| 4 | gggggagaaacgcggauuc | GAGCAAUCCCAGGCGCAUAGCUUCCGAGUAGACAGGAGGAGGGGUUGGAUGUGGCGUCUACUCGGUGUCGUG | aagcuucgcucuagaucucccuuuagugaggguua | 14 |
| lib4 32 | gggggagaaacgcggauccG | GCAACCCCAGGCGCAUAGCUUCCGAGUAGACAGGCGGAGCGGGUGGAUGUGGCGUC | ACGAGGaagcuucgcucuagaucucccuuuagugaggguua | 15 |
| lib8 9 | gggggagaaacgcggaucc | GCAAUCCCAGGCGCAUAGCUUCCGAGUAGACAGGAGGGGUGAGUGCGUCUACUCGGUCGU | Caagcuucgcucuagaucucccuuuagugaggguua | 16 |
| lib5 5 | gggggagaaacgcggauuc | GAGCAAUCCCAGGCGCAUAGCUUCCGAGUAGACAGGAGGGGAGGGGUGGAUGUGGCGUCUACUCGGUGUCGUCU | CGAGGaagcuucgcucuagaucucccuuuagugaggguua | 17 |
| 7 | gggggagaaacgcggauuc | GAGCAAGCCUGGCAUAGCUUCCGAGUAGACAGGAGGGGAGGGGUGGAUGUGGCGUCUACUCGGUGUCGUG | aagcuucgcucuagaucucccuuuagugaggguua | 18 |
| 48 | gggggagaaacgcggauccG | GCAAUCCCAGGCGCAUAGCUUCCGAGUAGACAGGAGGGGAGGGGUGGAUGUGGCGUCUGUGU | ACGAGGaagcuucgcucuagaucucccuuuagugaggguua | 19 |
| lib2 6 | gggggagaaacgcggauuc | GAGCAAUCCCAGGCGCAUAGCUUCCGAGUAGACAGGAGGGGAGGGGUGGAUGUGGCGUCU | CGAGaagcuucgcucuagaucucccuuuagugaggguua | 20 |
| lib6 23 | gggggagaaacgcggauuc | A AGCUUC GAGUAGACAGGAGGGGAGGGGUGGAUGUGGAGUCU | CGAGaagcuucgcucuagaucucccuuuagugaggguua | 21 |
| 4 | gggggagaaacgcggauccu | GAGCAAUCCCUAA GCAUAGCUUCCGAGUAGACAGGAGGGGAGGGGUGGAUGUGGCGUCU | CGAGaagcuucgcucuagaucucccuuuagugaggguua | 22 |
| lib7 21 | gggggagaaacgcggauuc | GAGCAAUCCCGGGCCAUAGCUUCCGAGGAGACAGGAGGGGGGUGGAUGUGGCGUCU | CGAGaagcuucgcucuagaucucccuuuagugaggguua | 23 |
| 43 | gggggagaaacgcggauuc | GAGCAAUCCCAGGCGCAUAGCUUCCGAGUAGACAGGCGGGGGGUGGAUGUGGCGUCU | CGAGaagcuucgcucuagaucucccuuuagugaggguua | 24 |
| Group A Boundary Experiments | | | | |
| lib3-13 boundaries 5' | GCUUCCGAGUAGACAGGAGGGGAGGGGUUGGAUGUGGCGUCUAC 3' | | | 25 |
| lib8-9 boundaries 5' | CUUCCGAGUAGACAGGAGGGGAGGGGUUGGAUGUGGCGUCUACUC 3' | | | 26 |
| lib4-32 boundary 5' | GGCAACCCCAGGCGCAUAGCUUCCGAGUAGACAGGCGGAGCGGGUGGAUGUGGCGUCACG 3' | | | 27 |
| Group B 5' CONSTANT | | VARIABLE | 3'CONSTANT | |
| lib4-12 | gggggagaaacgcggauccUGAGAAGGACGUCGGGGUCAACGGGGGUGCAGCAGUGCAGGCGCCGCACCACCAUGACCGCAGAAAAGGGCCGG | aagcuucgcucuagaucucccuuuagugaggguua | 28 |
| lib3-44 | gggggagaaacgcggauccUGAGAAGGACGUCGGGGUCAACGGGGGUGCAGCAGUGCAGGCGCCGCACCACCAUGACCGCAGAAAAGGGCCGG | aagcuucgcucuagaucucccuuuagugaggguua | 29 |
| lib3-42 | gggggagaaacgcggauccGGUUGGGAAA AUGUG GUAGAUU GUCGGAUU GACGGUGCAGCAGUGCAGGCGCCGCACCACCAUGACCGCAGAUAA | aagcuucgcucuagaucucccuuuagugaggguua | 30 |
| Group C 5'CONSTANT | | VARIABLE | 3' CONSTANT | |
| lib4-12 boundaries 5' | ggaaacgcggauccUGAGAAGGACGUCAGCAGAAAGGGCCGGCACCA 3' | | | 31 |
| lib1-20-3** | gggggagaaacgcggauccUGCUAGACCGAGGAUGCAAAGGGACAUGCAAAAGGGACCCUAUGUAUUAAGGAAACCGGCUCAGaagcuucgcucuagaucccuuuagugaggguua | | | 32 |
| lib1-20-3H**gggggagaaacgcggauccUGCUAGACCGAGGAUGCAAAGGGACAUGCAAAAGGGACCUAUGUAUAAGAACGCGGCUCCAGA | | | | 33 |
| lib6-30** gggggagaaacgcggauccUGCUAGACCGAGGAUGCAAAGGGACAUGCAAAAGGGACAUAGGAGGAAACCAU UAUAAGACAUGAGCAAUCUGGGAAACCUAU UAUAAGACAUGAGCAAUCGCCGGUCGCAG | aagcuucgcucuagaucucccuuuagugaggguua | | | 34 |

TABLE 3-continued

TGFβ Binding ligands

| | 5'CONSTANT | VARIABLE | 3'CONSTANT | |
|---|---|---|---|---|
| Group D. | | | | |
| lib2-6-1.* | gggggagaaacgcggaucc | UGUCUCCACCGCCGAUACUGGGGUUCCUGGGCCCUCCAUGCAGGAGGGGGUGGUUCCGAGAa | agcuucgcucuagaucucccuuuagugagggguua | 35 |
| lib2-6-1-81* | gggggagaaacgcggaucc | UGUCUCCACCGCCGAUACUGGGGUUCCUGGGCCCUCCAUGCAGGAGGGGGGUGGUUCCGAG | 3'CONSTANT | 36 |
| lib8-23* | gggggagaaacgcggaucc | UGUCUCCACCGCCGAUACUGGGUUCCUGGGGCCGCUCCAUGCAGGAGGGGGGUGGUUCCGAGAa | agcuucgcucuagaucucccuuuagugagggguua | 37 |
| lib9-10* | gggggagaaacgcggaucc | UGUCUCCACCGCCGAUACUGGGGUUCCUGGGGCCCUCCAUGCAGGAGGGG UGGUUCCGAGAa | agcuucgcucuagaucucccuuuagugagggguua | 38 |
| ORPHANS. | | | | |
| clone # | 5'CONSTANT | VARIABLE | 3'CONSTANT | |
| lib3-45 | gggggagaaacgcggaucc | CGAAGUCUGGUCUUUGGGAGUCCGCAUGCCCUGGCGAa | agcuucgcucuagaucucccuuuagugagggguua | 39 |
| lib1-20-5** | gggggagaaacgcggaucc | AAGAAUGUUCGGCCGCACGAGGUGCCGCACAGUGCGGUGCGAUACGGUCGAUUGGCCa | agcuucgcucuagaucucccuuuagugagggguua | 40 |
| lib1-20-12*** | gggggagaaacgcggaucc | GGUCACCCGGGCAUAUAACAAUGCCGACACUGGGACCUGGACGCGGUACCUGGACACUGGAAGa | agcuucgcucuagaucucccuuuagugagggguua | 41 |
| lib2-6-8**** | gggggagaaacgcggaucc | AUAACCGGCUGCAUGGGAGGACAUCCUGGAAAGGACGGGACUGGAGCAGUCCGAGAUGACGGUCGAGAUGACGGUCCGCa | agcuucgcucuagaucucccuuuagugagggguua | 42 |

Legend: The constant region of the ligand is shown in lower case and variable in upper. Sequences have been aligned. Deletions with respect to the first sequence in each group are shown by gaps, substitutions are in bold type.
*2NH₂—UTP, 2F—CTP.
**2F—UTP, 2F—CTP.
***2OH—UTP, 2OH—CTP
Group A and B bind with either 2NH₂— or 2F— pyrimidines.
Ligands bind with either 2NH₂— or 2F— pyrimidines unless otherwise indicated.

TABLE 4

| Group | Ligand | $B_{max}$ | $K_d$ | $IC_{50}$ |
|---|---|---|---|---|
| A | lib3-13 | 0.60 | 0.9 nM | 9.7 nM |
|   |         | 0.38 | 0.7 nM | 42 nM |
|   |         | 0.55 | 0.9 nM | 18 nM |
|   |         |      |        | 32 nM |
|   | lib3-3  | 0.44 | 1.7 nM | NT |
|   | lib4-32 | 0.50 | 0.8 nM | 20 nM |
|   |         |      |        | 157 nM |
|   | lib5-5  | 0.37 | 2.4 nM | 49 nM |
|   | lib5-7  | 0.33 | 3.4 nM | 17 nM |
|   | lib8-9  | 0.4  | 1.7 nM | 210 nM |
|   | lib8-9* | 0.35 | 2.8 nM | 124 nM |
|   | lib5-48 | 0.32 | 3.8 nM | not inhibitory |
|   | lib2-6-4 | 0.20 | 3.1 nM | not inhibitory |
|   | lib6-23 | 0.35 | 3.4 nM | not inhibitory |
|   | lib7-21**** | 0.18 | 2.4 nM | not inhibitory |
|   | lib7-43**** | 0.33 | 3.3 nM | not inhibitory |
| B | lib4-12 | 0.15 | 0.4 nM | 109 nM |
|   |         | 0.08 | 0.2 nM | 108 nM |
|   |         |      |        | 69 nM |
|   | lib3-44 | 0.18 | 1.3 nM | 119 nM |
|   | lib3-42 | 0.16 | 0.6 nM | 22 nM |
| C | lib1-20-3** | 0.67 | 30 nM | not inhibitory |
|   | lib1-20-3-82** | 0.46 | 6.1 nM | not inhibitory |
|   | lib6-30** | 0.35 | 8.8 nM | not inhibitory |

TABLE 4-continued

| Group | Ligand | $B_{max}$ | $K_d$ | $IC_{50}$ |
|---|---|---|---|---|
| D | lib2-6-1* | 0.40 | 14.3 nM | 112 nM |
|   |           |      |         | 103 nM |
|   | lib2-6-1-81* | 0.39 | 10.7 nM | 201 nM |
|   |           |      |         | 298 nM |
|   | lib8-23*  | 0.48 | 6.6 nM | not inhibitory |
|   | lib9-10*  | 0.24 | 1.1 nM | not inhibitory |
| Orphans | lib3-45 | 0.08 | 1.9 nM | not inhibitory |
|   | lib1-20-5** | 0.42 | 46 nM | not inhibitory |
|   | lib1-20-12*** | 0.34 | 3.1 nM | NT |
|   | lib1-6-8*** | 0.12 | 4.7 nM | NT |
| Controls | lib5-9 |  | nonbinder | not inhibitory |
|   | random 64N6 |  | nonbinder | not inhibitory | ligands are 2'-NH2 pyrimidines unless otherwise noted
*2'-NH2-UTP, 2'-F-CTP,
**2'-F pyrimidines,
***2'-OH pyrimidines,
****2'-F-UTP, 2'-NH2-CTP

TABLE 5

DNA oligonucleotides used in Examples 5 and 6*

| Description | | Sequence | SEQ. ID NO. |
|---|---|---|---|
| 40N7 | Template for RNA SELEX | TCGGGCGAGTCGTCTG[40N]CCGCATCGTCCTCCC | 43 |
| 5N7 | 5'-primer for PCR | TAATACGACTCACTATAGGGAGGACGATGCGG | 44 |
| 3N7 | 3'-primer for PCR | TCGGGCGAGTCGTCTG | 45 |
| 40D7 | Starting material for DNA SELEX | GGGAGGACGATGCGG[40N]CAGACGACTCGCCCGA | 46 |
| 5D7 | 5'-primer for PCR | GGGAGGACGATGCGG | 47 |
| 3D7 | 3'-primer for PCR | (biotin)₃TCGGGCGAGTCGTCTG | 48 |
| 40N8 | Template for RNA SELEX | GCCTGTTGTGAGCCTCCTGTCGAA[40N]TTGAGCGTTTATTCTTGTCTCCC | 49 |
| 5N8 | 5'-primer for PCR | TAATACGACTCACTATAGGGAGACAAGAATAAACGCTCAA | 50 |
| 3N8 | 3'-primer for PCR | GCCTGTTGTGAGCCTCCTGTCGAA | 51 |
| 40D8 | Starting material for DNA SELEX | GGGAGACAAGAATAAACGCTCAA[40N]TTCGACAGGAGGCTCACAACAGGC | 52 |
| 5D8 | 5'-primer for PCR | GGGAGACAAGAATAAACGCTCAA | 53 |
| 3D8 | 3'-primer for PCR | (biotin)₃GCCTGTTGTGAGCCTCCTGTCGAA | 54 |

*DNA oligonucleotides 40N7 and 40N8 were used to generate the double-stranded DNA template for in vitro transcription. The 3'-primers 3N7 and 3N8 were also used to generate cDNA from the RNA repertoire. Synthetically synthesized DNA oligonucleotides 40D7 and 40D8 were used directly as the starting repertoire for the two single-stranded DNA SELEX experiments. PCR amplification of the selected repertoires used the appropriate 5'- or 3'-primer. The symbol 40N indicated a 40-nucleotide randomized region within the oligonucleotide.

TABLE 6

TGFβ1 40N7 DNA Selex Sequence of fifty randomly chosen clones.

| | | SEQ. ID NO. |
|---|---|---|
| Group A | | |
| 20 (11 clones) | CCAGGGGGGGTATGGGGGTGGTGCTACTTACTTGCGTCTT | 55 |
| 4 | CCAGGGGGGGTATGGGGGTAGTGCTACTTACTTGCGTCTT | 56 |
| 5 | CCAGGGGGGGTATGGGGGTAGTACTACTTACTTACGTCTT | 57 |
| 8 | CCAGGGGGGGTATGGGGGTATACTACTTACTTACGTCTT | 58 |
| 13 | CCAGGGGGGGTATGGGGGTAATACTACTTACTTACATCTT | 59 |
| 16 | CCAGGGGGGGTATGGGGGTAATACTACTTACTTACGTCTT | 60 |
| 40 | CCAGGGGGGGTATGGGGGTGGTGTTACTTACTTGCGTCTT | 61 |
| 48 | CCAGGGGGGGTATGGGGGTGGTGCTTCTTACTTGCGTCTT | 62 |
| Group B | | |
| 18 | CCAGGGGGGGTATGGGGGTGGTGTACTTTTTCCTGCGTCTTC | 63 |
| 19 | CCAGGGGGGGTATGGGGGTGGTTCGTTTTTCTTTGCGGCTT | 64 |
| 32 | CCAGGGGGGGTGTGGGGGTGGTGTACTTTTTCTTGTCTTC | 65 |
| 46 | CCAGGGGGGGTATGGGGGTGGTTTGGTATGTTGCGTCCGT | 66 |
| Group C | | |
| 12 (3 clones) | CCGGGGTGGGTATGGGGGTAATACTACTTACTTACGTCTT | 67 |
| 1 | CCGGGGGTGGGTAGGGGGGTAGTGCTACTTACTTACGTCTT | 68 |
| 3 | CCAGGGTCGGTGTGGGGGTAGTACTACTTACTTGCGTCTT | 69 |
| 10 | CCAGGGTGGGTATGGGGGTAGTGCTACTTACTTGCGTCTT | 70 |
| 23 | CCGGGGTGGGTATGGGGGTGGTGCTACTTACTTGCGTCTT | 71 |
| 34 | CCTGGGTGGGTATGGGGGTGGTGCTACTTACTTGCGTCTT | 72 |
| Group D | | |
| 2 | CCACGGGTGGGTGTGGGGTAGTGTGTCTCACTTTACATCAC | 73 |
| 6 | CCCGGGGTGGGTGTGGGGTAGTGTATTATATTTACAGCCT | 74 |
| 25 & 38 | CCAGGGTCGGTGTGGGGTGGTGTACTTTTTCCTGTCCTTC | 75 |
| 7 | CCAGGGTCGGTATGGGGTAGTGTACTTTTTAATGATCTTC | 76 |
| 9 | CCCGGGGGAGAGCGGTGGGTAGTGTTCTATAGTATTCGTGT | 77 |
| 11 | CCAGGGGGGGTATGTTTTAATACTACTTACTTACGTCTT | 78 |
| 17 | CCAGGGAGGGTATGGGGGTGGTGTTTCTAGTTTTGCGGCGT | 79 |
| 21 | CCAGGGTGGGCATGGGGGTGGTGTGGATTAATTCTTCGTCC | 80 |
| 24 | CCAGGGTCGGTGTGGGGTGGTGTTTTTATTTACTCGTCGC | 81 |
| 28 & 30 | GGGGCGGCTTGGAAGAGGTTGCCGGTTGGAGTATTCGAGC | 82 |
| 29 | CCAGGTGTGGGGTGGTTTGGGTTTTCTTTCGTCGCC | 83 |
| 31 | CCAGGGTGGGTATGGGGGTTTAATTAATTCTTCGTCCCA | 84 |
| 35 | GGGGCGGCTTGGAAGAGGTTGCCGGTTGGAGTATTCGAGC | 85 |
| 36 | CCCGGGGTGGGTGTGGGGTGGTGTGAATTAATTCTTCGTCC | 86 |
| 41 | CCCGGGGTGGGTGTGGGGTGGTGTATTATATTTGCGGCCT | 87 |
| 44 & 45 | CCAGGGTCGGTGTGGGGTGGTGTACTTTTTCCTGTCCTTC | 88 |
| 50 | GGGGCGGCTTGGAAGAGGTTGCCGGTTGGAGTATTCGAGC | 89 |

Bold typeface indicates a discrepancy with the most common sequence of that group.

---

We claim:

1. A method of identifying nucleic acid ligands to transforming growth factor beta (TGFβ) comprising:
   a) preparing a candidate mixture of nucleic acids;
   b) contacting the candidate mixture of nucleic acids with TGFβ, wherein nucleic acids having an increased affinity to TGFβ relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acid sequences with relatively higher affinity and specificity for binding to TGFβ, whereby nucleic acid ligands of TGFβ may be identified.

2. The method of claim 1 further comprising:
   e) repeating steps b), c), and d).

3. The method of claim 1 wherein said candidate mixture of nucleic acids is comprised of single stranded nucleic acids.

4. The method of claim 3 wherein said single stranded nucleic acids are ribonucleic acids.

5. The method of claim 4 wherein said nucleic acids comprise 2'-amino (2'-$NH_2$) modified ribonucleic acids.

6. The method of claim 4 wherein said nucleic acids comprise 2'-F modified ribonucleic acids.

7. The method of claim 4 wherein said nucleic acids comprise 2'-$NH_2$-UTP, 2'-F-CTP modified ribonucleic acids.

8. The method of claim 4 wherein said nucleic acids comprise 2'-F-UTP, 2'-$NH_2$-CTP modified ribonucleic acids.

9. The method of claim 3 wherein said single stranded nucleic acids are deoxyribonucleic acids.

* * * * *

SEQUENCE LISTING ( 1 ) GENERAL INFORMATION:

( i i i ) NUMBER OF SEQUENCES: 89

( 2 ) INFORMATION FOR SEQ ID NO: 1:

( i ) SEQUENCE CHARACTERISTICS:
( A ) LENGTH: 117 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 1:

| | | | | |
|---|---|---|---|---|
| GGGGGAGAAC | GCGGAUCCNN | NNNNNNNNNN | NNNNNNNNNN | NNNNNNNNNN | 50 |
| NNNNNNNNNN | NNNNNNNNNN | NNNNNNNNNN | NNAAGCUUCG | CUCUAGAUCU | 100 |
| CCCUUUAGUG | AGGGUUA | | | | 117 |

( 2 ) INFORMATION FOR SEQ ID NO: 2:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 2:

```
GGGGGAGAAC  GCGGAUCCNN  NNNNNNNNNN  NNNNNNNNNN  NNNNNNNNNN        50
NNNNNNNNAA  GCUUCGCUCU  AGAUCCCCU   UUAGUGAGGG  UUA               93
```

( 2 ) INFORMATION FOR SEQ ID NO: 3:

( i ) SEQUENCE CHARACTERISTICS:
    ( A ) LENGTH: 123 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO: 3:

```
GGGGGAGAAC  GCGGAUCCUG  UCUCCACCGC  CGAUACUGGG  GUUCCUGGGG       50
CCCCUCCAUG  GAGGAGGGGG  GAGGGGUGG   UUCGGAGAAA  GCUUCGCUCU      100
GAAUCUCCCU  UUAGUGAGGG  UUA                                     123
```

( 2 ) INFORMATION FOR SEQ ID NO: 4:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 4:

```
GGGAGAACGC  GGATCCNNNN  NNNNNNNNNN  NNNNNNNNNN  NNNNNNNNNN        50
NNNNNNNNNN  NNNNNNNNNN  NNNNNNNNNN  AAGCTTCGCT  CTAGA             95
```

( 2 ) INFORMATION FOR SEQ ID NO: 5:

( i ) SEQUENCE CHARACTERISTICS:
    ( A ) LENGTH: 71 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 5:

```
GGGAGAACGC  GGATCCNNNN  NNNNNNNNNN  NNNNNNNNNN  NNNNNNNNNN        50
NNNNNNAAGC  TTCGCTCTAG  A                                         71
```

( 2 ) INFORMATION FOR SEQ ID NO: 6:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 6:

GGGGGAGAAC GCGGATCCTG TCTCCACCGC CGATACTGGG GTTCCTGGGG    50

CCCCTCCATG GAGGAGGGGG TGGTTCGGAG AAAGCTTCGC TCTAG    95

( 2 ) INFORMATION FOR SEQ ID NO: 7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 7:

TAATACGACT CACTATAGGG GGAGTCTGCG GATCC    35

( 2 ) INFORMATION FOR SEQ ID NO: 8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 8:

TAATACGACT CACTATAGGG GGAGAACGCG GATCC    35

( 2 ) INFORMATION FOR SEQ ID NO: 9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 9:

TAACCCTCAC TAAAGGGAGA TCTAGAGCGA AGCTT    35

( 2 ) INFORMATION FOR SEQ ID NO: 10:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 10:

GATTTAGGTG ACACTATAGA ATATGCATCA CTAGTAAGCT TTGCTCTAGA    50

( 2 ) INFORMATION FOR SEQ ID NO: 11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 11:

GGATCCCGGA GCTCCCTATA GTGAGTCGTA TTA                                    33

( 2 ) INFORMATION FOR SEQ ID NO: 12:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 12:

GGGGGAGAAC GCGGAUCCGA GCAAUCCCAG GCGCAUAGCU UCCGAGUAGA                  50

CAGGAGGGAG GGUGGAUGU GGCGUCUACU CGGUGUCGUG AAGCUUCGCU                   100

CUAGAUCUCC CUUUAGUGAG GGUUA                                            125

( 2 ) INFORMATION FOR SEQ ID NO: 13:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 13:

GGGGGAGAAC GCGGAUCCGA GCAACCCCAG GCGCAUAGCU UCCGAGUAGA                  50

CAGGAGGGAG GGUGGAUGU GGCGUCUACU CGGUGUCGUG AAGCUUCGCU                   100

CUAGAUCUCC CUUUAGUGAG GGUUA                                            125

( 2 ) INFORMATION FOR SEQ ID NO: 14:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 14:

GGGGAGAAC GCGGAUCCGA GCAACCCCAG GCGCAUAGCU UCCGAGUAGA                   50

CAGGCGGGAG GGUGGAUGU GGCGUCUACU CGGAGUCGUG AAGCUUCGCU                   100

CUAGAUCUCC CUUUAGUGAG GGUUA                                            125

( 2 ) INFORMATION FOR SEQ ID NO: 15:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
( D ) OTHER INFORMATION: All pyrimidines are 2'-amino
( 2 ' N H 2 )modified ( x i ) SEQUENCE DESCRIPTION: SEQ ID NO: 15:

| GGGGGAGAAC | GCGGAUCCGG | CAACCCCAGG | CGCAUAGCUU | CCGAGUAGAC | 50 |
| AGGCGGGAGG | GGUGGAUGUG | GCGUCACGAG | GAAGCUUCGC | UCUAGAUCUC | 100 |
| CCUUUAGUGA | GGGUUA | | | | 116 |

( 2 ) INFORMATION FOR SEQ ID NO: 16:

( i ) SEQUENCE CHARACTERISTICS:
( A ) LENGTH: 123 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 16:

| GGGGGAGAAC | GCGGATCCGC | AAUCCCAGGC | GCAUAGCUUC | CGAGUAGACA | 50 |
| GGAGGGAGGG | GUGGAUGUGG | CGUCUACUCG | GCGUCGUGAA | GCUUCGCUCU | 100 |
| AGAUCUCCCU | UUAGUGAGGG | UUA | | | 123 |

( 2 ) INFORMATION FOR SEQ ID NO: 17:

( i ) SEQUENCE CHARACTERISTICS:
( A ) LENGTH: 117 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-amino
( 2 ' N H 2 )modified ( x i ) SEQUENCE DESCRIPTION: SEQ ID NO: 17:

| GGGGGAGAAC | GCGGAUCCGA | GCAAUCCCAG | GCGCAUAGCU | UCCGAGUAGA | 50 |
| CAGGAGGGAG | GGUGGAUGU | GGCGUCUCGA | GGAAGCUUCG | CUCUAGAUCU | 100 |
| CCCUUUAGUG | AGGGUUA | | | | 117 |

( 2 ) INFORMATION FOR SEQ ID NO: 18:

( i ) SEQUENCE CHARACTERISTICS:
( A ) LENGTH: 123 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-amino
( 2 ' N H 2 )modified ( x i ) SEQUENCE DESCRIPTION: SEQ ID NO: 18:

| GGGGGAGAAC | GCGGAUCCGA | GCAAGCCCUG | GCAUAGCUUC | CGAGUAGACA | 50 |
| GGAGGGAGGG | GUGGAUGUGG | CGUCUACUCG | GUGUCGUGAA | GCUUCGCUCU | 100 |
| AGAUCUCCCU | UUAGUGAGGG | UUA | | | 123 |

( 2 ) INFORMATION FOR SEQ ID NO: 19:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-amino
            ( 2 ' N H 2 )modified ( x i ) SEQUENCE DESCRIPTION: SEQ ID NO: 19:

```
GGGGGAGAAC  GCGGAUCCGG  CAAUCCCAGG  CGCAUAGCUU  CCGAGUAGAC      50
AGGAGGGAGG  GGUGGAUGUG  GUGUACGAGG  AAGCUUCGCU  CUAGAUCUCC     100
CUUUAGUGAG  GGUUA                                              115
```

( 2 ) INFORMATION FOR SEQ ID NO: 20:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 20:

```
GGGGGAGAAC  GCGGAUCCGA  GCAAUCCCAG  GCGCAUAGCU  UCCGAGUAGA      50
CAGGAGGGAG  GGUGGAUGU   GGUGUCUCGA  GAAGCUUCGC  UCUAGAUCUC     100
CCUUUAGUGA  GGGUUA                                             116
```

( 2 ) INFORMATION FOR SEQ ID NO: 21:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 21:

```
GGGGGAGAAC  GCGGAUCCAA  GCUUCGAGUA  GACAGGAGGG  AGGGGUGGAU      50
GUGGAGUCUC  GAGAAGCUUC  GCUCUAGAUC  UCCCUUUAGU  GAGGGUUA        98
```

( 2 ) INFORMATION FOR SEQ ID NO: 22:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 22:

-continued

```
GGGGGAGAAC  GCGGAUCCGA  GCAAUCCUAA  GCAUAGCUUC  GAGUAGACAG        50

GAGGGAGGGG  UGGAUGUGGC  GUCUCGAGAA  GCUUCGCUCU  AGAUCUCCCU        100

UUAGUGAGGG  UUA                                                   113
```

(2) INFORMATION FOR SEQ ID NO: 23:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-F uracil (ix) FEATURE:
        (D) OTHER INFORMATION: All C's are 2'NH2 cytosine (xi) SEQUENCE DESCRIPTION: SEQ ID NO: 23:

```
GGGGGAGAAC  GCGGAUCCGA  GCAAUCCCGG  GCGCAUAGCU  UCCGAGGAGA        50

CAGGCGGGAG  GGGUGGAUGU  GGCGUCUCGA  GAAGCUUCGC  UCUAGAUCUC        100

CCUUUAGUGA  GGGUUA                                                116
```

(2) INFORMATION FOR SEQ ID NO: 24:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All U's are 2'-F uracil (ix) FEATURE:
        (D) OTHER INFORMATION: All C's are 2'NH2 cytosine (xi) SEQUENCE DESCRIPTION: SEQ ID NO: 24:

```
GGGGGAGAAC  GCGGAUCCGA  GCAAUCCCAG  GCGCAUAGCU  UCCGAGUAGA        50

CAGGCGGGAG  GGGUGGAUGU  GGCGUCUCGA  GAAGCUUCGC  UCUAGAUCUC        100

CCUUUAGUGA  GGGUUA                                                116
```

(2) INFORMATION FOR SEQ ID NO: 25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: All pyrimidines are 2'Fluoro
            (2'-F) modified (xi) SEQUENCE DESCRIPTION: SEQ ID NO: 25:

```
GCUUCCGAGU  AGACAGGAGG  GAGGGUGGA   UGUGGCGUCU  AC                42
```

(2) INFORMATION FOR SEQ ID NO: 26:

(i) SEQUENCE CHARACTERISTICS:
        (A) LENGTH: 43 base pairs ( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 26:

CUUCCGAGUA GACAGGAGGG AGGGGUGGAU GUGGCGUCUA CUC    43

( 2 ) INFORMATION FOR SEQ ID NO: 27:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-amino
( 2 ' N H 2 )modified ( x i ) SEQUENCE DESCRIPTION: SEQ ID NO: 27:

GGGGGAGAAC GCGGAUCCGG CAACCCCAGG CGCAUAGCUU CCGAGUAGAC    50

AGGCGGGAGG GGUGGAUGUG GCGUCACG    78

( 2 ) INFORMATION FOR SEQ ID NO: 28:

( i ) SEQUENCE CHARACTERISTICS:
( A ) LENGTH: 117 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'-amino
( 2 ' N H 2 )modified ( x i ) SEQUENCE DESCRIPTION: SEQ ID NO: 28:

GGGGGAGAAC GCGGAUCCUG AGAAGGACGU CGGGGUCAAC GGGGUGAGGU    50

GCAGCAGAAA GGGCCGGCAC CACAUGACGU AAAAGCUUCG CUCUAGAUCU    100

CCCUUUAGUG AGGGUUA    117

( 2 ) INFORMATION FOR SEQ ID NO: 29:

( i ) SEQUENCE CHARACTERISTICS:
( A ) LENGTH: 108 base pairs
( B ) TYPE: nucleic acid
( C ) STRANDEDNESS: single
( D ) TOPOLOGY: linear ( i i ) MOLECULE TYPE: RNA ( i x ) FEATURE:
( D ) OTHER INFORMATION: All pyrimidines are 2'Fluoro
( 2 ' - F )modified ( x i ) SEQUENCE DESCRIPTION: SEQ ID NO: 29:

GGGGGAGAAC GCGGAUCCUG AGAAGGACGU CGGGGUGAGG UGCAGCAGAA    50

AGGGCCGGCA CCACAUGACG UAAAAGCUUC GCUCUAGAUC UCCCUUUAGU    100

GAGGGUUA    108

( 2 ) INFORMATION FOR SEQ ID NO: 30:

( i ) SEQUENCE CHARACTERISTICS:
        ( A ) LENGTH: 92 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 30:

```
GGGGGAGAAC GCGGAUCCGG UGGGAAAGUC GGAUUAUGUG UGUAGAUUUG        50
UGUGCGAAAG CUUCGCUCUA GAUCUCCCUU UAGUGAGGGU UA                92
```

( 2 ) INFORMATION FOR SEQ ID NO: 31:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'-amino
            ( 2 ' N H 2 )modified ( x i ) SEQUENCE DESCRIPTION: SEQ ID NO: 31:

```
GGAGAACGCG GAUCCUGAGA AGGACGUCGG GGUCAACGGG GUGAGGUGCA        50
GCAGAAAGGG CCGGCACCA                                          69
```

( 2 ) INFORMATION FOR SEQ ID NO: 32:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 32:

```
GGGGGAGAAC GCGGAUCCUG CUAGACCGAG GAUGCAAAGG GACAUGCAUU        50
AGGGAAACCU AUGUAUAAGA ACGCGGUCGC AGAAGCUUCG CUCUAGAUCU       100
CCCUUUAGUG AGGGUUA                                           117
```

( 2 ) INFORMATION FOR SEQ ID NO: 33:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 33:

```
GGGGGAGAAC GCGGAUCCUG CUAGACCGAG GAUGCAAAGG GACAUGCAUU      50

AGGGAAACCU AUGUAUAAGA ACGCGGUCGC AGA                        83
```

( 2 ) INFORMATION FOR SEQ ID NO: 34:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All pyrimidines are 2'Fluoro
            ( 2 ' - F )modified ( x i ) SEQUENCE DESCRIPTION: SEQ ID NO: 34:

```
GGGGGAGAAC GCGGAUCCUG CUAGACCGAG GAUGCAAAGG GACAUGCAUU      50

AGGGAAACCU AUUAUAAGAA CGCGGUCGCA GAAGCUUCGC UCUAGAUCUC     100

CCUUUAGUGA GGGUUA                                          116
```

( 2 ) INFORMATION FOR SEQ ID NO: 35:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-F cytosine ( i x ) FEATURE:
        ( D ) OTHER INFORMATION: All U's are 2'NH2 uracil ( x i ) SEQUENCE DESCRIPTION: SEQ ID NO: 35:

```
GGGGGAGAAC GCGGAUCCUG UCUCCACCGC CGAUACUGGG GUUCCUGGGG      50

CCCCUCCAUG CAGGAGGGGG GUGGUUCGGA GAAAGCUUCG CUCUAGAUCU     100

CCCUUUAGUG AGGGUUA                                         117
```

( 2 ) INFORMATION FOR SEQ ID NO: 36:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: All C's are 2'-F cytosine ( i x ) FEATURE:
        ( D ) OTHER INFORMATION: All U's are 2'NH2 uracil ( x i ) SEQUENCE DESCRIPTION: SEQ ID NO: 36:

```
GGGGGAGAAC GCGGAUCCUG UCUCCACCGC CGAUACUGGG GUUCCUGGGG      50

CCCCUCCAUG CAGGAGGGGG GUGGUUCGGA G                          81
```

( 2 ) INFORMATION FOR SEQ ID NO: 37:

( i ) SEQUENCE CHARACTERISTICS:

( A ) LENGTH: 117 base pairs
                    ( B ) TYPE: nucleic acid
                    ( C ) STRANDEDNESS: single
                    ( D ) TOPOLOGY: linear ( i i ) MOLECULE TYPE: RNA ( i x ) FEATURE:
                    ( D ) OTHER INFORMATION: All C's are 2'-F cytosine ( i x ) FEATURE:
                    ( D ) OTHER INFORMATION: All U's are 2'NH2 uracil ( x i ) SEQUENCE DESCRIPTION: SEQ ID NO: 37:

GGGGGAGAAC GCGGAUCCUG UCUCCACCGC CGAUACUGGG GUUCCUGGGG         50

CCGCUCCAUG CAGGAGGGGG GUGGUUCGGA GAAAGCUUCG CUCUAGAUCU         100

CCCUUUAGUG AGGGUUA                                             117

( 2 ) INFORMATION FOR SEQ ID NO: 38:

( i ) SEQUENCE CHARACTERISTICS:
                    ( A ) LENGTH: 115 base pairs
                    ( B ) TYPE: nucleic acid
                    ( C ) STRANDEDNESS: single
                    ( D ) TOPOLOGY: linear ( i i ) MOLECULE TYPE: RNA ( i x ) FEATURE:
                    ( D ) OTHER INFORMATION: All C's are 2'-F cytosine ( i x ) FEATURE:
                    ( D ) OTHER INFORMATION: All U's are 2'NH2 uracil ( x i ) SEQUENCE DESCRIPTION: SEQ ID NO: 38:

GGGGGAGAAC GCGGAUCCUG UCUCCACCGC CGAUACUGGG GUUCCUGGGG         50

CCCCUCCAUG CAGGAGGGGU GGUUCGGAGA AAGCUUCGCU CUAGAUCUCC         100

CUUUAGUGAG GGUUA                                               115

( 2 ) INFORMATION FOR SEQ ID NO: 39:

( i ) SEQUENCE CHARACTERISTICS:
                    ( A ) LENGTH: 92 base pairs
                    ( B ) TYPE: nucleic acid
                    ( C ) STRANDEDNESS: single
                    ( D ) TOPOLOGY: linear ( i i ) MOLECULE TYPE: RNA ( i x ) FEATURE:
                    ( D ) OTHER INFORMATION: All pyrimidines are 2'Fluoro
                        ( 2 ' - F )modified ( x i ) SEQUENCE DESCRIPTION: SEQ ID NO: 39:

GGGGAGAAC GCGGAUCCGG AAGUCUGGUC UUUGGGGAGU CCGCAUGGCC          50

CUGGCGAAAG CUUCGCUCUA GAUCUCCCUU UAGUGAGGGU UA                 92

( 2 ) INFORMATION FOR SEQ ID NO: 40:

( i ) SEQUENCE CHARACTERISTICS:
                    ( A ) LENGTH: 111 base pairs
                    ( B ) TYPE: nucleic acid
                    ( C ) STRANDEDNESS: single
                    ( D ) TOPOLOGY: linear ( i i ) MOLECULE TYPE: RNA ( i x ) FEATURE:
                    ( D ) OTHER INFORMATION: All pyrimidines are 2'Fluoro (2'-F)modified (xi) SEQUENCE DESCRIPTION: SEQ ID NO: 40:

```
GGGGGAGAAC GCGGAUCCAA GAAUGUUCGG CCGCACGAGG UGACAGUGGU        50
GCGGAUACGG ACCGAUUGGG UUUGCCAAGC UUCGCUCUAG AUCUCCCUUU       100
AGUGAGGGUU A                                                 111
```

(2) INFORMATION FOR SEQ ID NO: 41:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 41:

```
GGGGGAGAAC GCGGAUCCGG UCACCCGGGC AUAUAACAAU GCCGACACUG        50
GGGUACCUGG GACGGGUGGG ACUGGACGGA AGAAGCUUCG CUCUAGAUCU       100
CCCUUUAGUG AGGGUUA                                           117
```

(2) INFORMATION FOR SEQ ID NO:42:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO: 42:

```
GGGGGAGAAC GCGGAUCCAU AACCGGCUGC AUGGGAGGGA CAUCCUGGGA        50
AAGGACGGGU CGAGAUGACC UGAGCAGUUC CGGCAAGCUU CGCUCUAGAU       100
CUCCCUUUAG UGAGGGUUA                                         119
```

(2) INFORMATION FOR SEQ ID NO: 43:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

```
TCGGGCGAGT CGTCTGNNNN NNNNNNNNNN NNNNNNNNNN NNNNNNNNNN        50
NNNNNNCCGC ATCGTCCTCC C                                       71
```

(2) INFORMATION FOR SEQ ID NO: 44:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

```
TAATACGACT CACTATAGGG AGGACGATGC GG                           32
```

(2) INFORMATION FOR SEQ ID NO: 45:

(i) SEQUENCE CHARACTERISTICS:
(A) LENGTH: 16 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 45:

TCGGGCGAGT CGTCTG                                                                                                  16

(2) INFORMATION FOR SEQ ID NO: 46:

(i) SEQUENCE CHARACTERISTICS:
(A) LENGTH: 71 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 46:

GGGAGGACGA TGCGGNNNNN NNNNNNNNNN NNNNNNNNNN NNNNNNNNNN                                  50

NNNNNCAGAC GACTCGCCCG A                                                                                             71

(2) INFORMATION FOR SEQ ID NO: 47:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 47:

GGGAGGACGA TGCGG                                                                                                    15

(2) INFORMATION FOR SEQ ID NO: 48:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (ix) FEATURE:
(D) OTHER INFORMATION: N at positions 1-3 is biotin (xi) SEQUENCE DESCRIPTION: SEQ ID NO: 48:

NNNTCGGGCG AGTCGTCTG                                                                                                19

(2) INFORMATION FOR SEQ ID NO: 49:

(i) SEQUENCE CHARACTERISTICS:
(A) LENGTH: 87 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 49:

GCCTGTTGTG AGCCTCCTGT CGAANNNNNN NNNNNNNNNN NNNNNNNNNN                                  50

```
NNNNNNNNNN NNNNTTGAGC GTTTATTCTT GTCTCCC                            87
```

(2) INFORMATION FOR SEQ ID NO: 50:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 50:

```
TAATACGACT CACTATAGGG AGACAAGAAT AAACGCTCAA                         40
```

(2) INFORMATION FOR SEQ ID NO: 51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 51:

```
GCCTGTTGTG AGCCTCCTGT CGAA                                          24
```

(2) INFORMATION FOR SEQ ID NO: 52:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 52:

```
GGGAGACAAG AATAAACGCT CAANNNNNNN NNNNNNNNNN NNNNNNNNNN              50
NNNNNNNNNN NNNTTCGACA GGAGGCTCAC AACAGGC                            87
```

(2) INFORMATION FOR SEQ ID NO: 53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 53:

```
GGGAGACAAG AATAAACGCT CAA                                           23
```

(2) INFORMATION FOR SEQ ID NO: 54:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (ix) FEATURE:
        (D) OTHER INFORMATION: N at positions 1-3 is biotin (xi) SEQUENCE DESCRIPTION: SEQ ID NO: 54:

NNNGCCTGTT GTGAGCCTCC TGTCGAA 27

(2) INFORMATION FOR SEQ ID NO: 55:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 55:

GGGAGGACGA TGCGGCCAGG GGGGGTATGG GGGTGGTGCT ACTTACTTGC 50

GTCTTCAGAC GACTCGCCCG A 71

(2) INFORMATION FOR SEQ ID NO: 56:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 56:

GGGAGGACGA TGCGGCCAGG GGGGGTATGG GGGTAGTGCT ACTTACTTGC 50

GTCTTCAGAC GACTCGCCCG A 71

(2) INFORMATION FOR SEQ ID NO: 57:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 57:

GGGAGGACGA TGCGGCCAGG GGGGGTATGG GGGTAGTACT ACTTACTTAC 50

GTCTTCAGAC GACTCGCCCG A 71

(2) INFORMATION FOR SEQ ID NO: 58:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 58:

GGGAGGACGA TGCGGCCAGG GGGGGTATGG GGGTATACTA CTTACTTACG 50

TCTTCAGACG ACTCGCCCGA 70

(2) INFORMATION FOR SEQ ID NO: 59:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA ( x i ) SEQUENCE DESCRIPTION: SEQ ID NO: 59:

GGGAGGACGA TGCGGCCAGG GGGGGTATGG GGGTAATACT ACTTACTTAC 50

ATCTTCAGAC GACTCGCCCG A 71

( 2 ) INFORMATION FOR SEQ ID NO: 60:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 60:

GGGAGGACGA TGCGGCCAGG GGGGGTATGG GGGTAATACT ACTTACTTAC 50

GTCTTCAGAC GACTCGCCCG A 71

( 2 ) INFORMATION FOR SEQ ID NO: 61:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 61:

GGGAGGACGA TGCGGCCAGG GGGGGTATGG GGGTGGTGTT ACTTACTTGC 50

GTCTTCAGAC GACTCGCCCG A 71

( 2 ) INFORMATION FOR SEQ ID NO: 62:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 62:

GGGAGGACGA TGCGGCCAGG GGGGGTATGG GGGTGGTGCT TCTTACTTGC 50

GTCTTCAGAC GACTCGCCCG A 71

( 2 ) INFORMATION FOR SEQ ID NO: 63:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 63:

GGGAGGACGA TGCGGCCAGG GGGGGTATGG GGGTGGTGTA CTTTTTCCTG 50

CGTCTTCCAG ACGACTCGCC CGA 73

( 2 ) INFORMATION FOR SEQ ID NO: 64:

( i ) SEQUENCE CHARACTERISTICS:
        ( A ) LENGTH: 72 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 64:

GGGAGGACGA TGCGGCCAGG GGGGGTATGG GGGTGGTTCG TTTTTCTTTG    50

CGGCTTCAGA CGACTCGCCC GA    72

(2) INFORMATION FOR SEQ ID NO: 65:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 65:

GGGAGGACGA TGCGGCCAGG GGGGGTGTGG GGGTGGTGTA CTTTTTCTTG    50

TCTTCCAGAC GACTCGCCCG A    71

(2) INFORMATION FOR SEQ ID NO: 66:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 66:

GGGAGGACGA TGCGGCCAGG GGGGGTATGG GGGTGGTTTG GTATGTTGCG    50

TCCGTCAGAC GACTCGCCCG A    71

(2) INFORMATION FOR SEQ ID NO: 67:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 67:

GGGAGGACGA TGCGGCCGGG GTGGGTATGG GGGTAATACT ACTTACTTAC    50

GTCTTCAGAC GACTCGCCCG A    71

(2) INFORMATION FOR SEQ ID NO:68 :

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 68:

GGGAGGACGA TGCGGCCGGG GGTGGGTAGG GGGGTAGTGC TACTTACTTA    50

CGTCTTCAGAC GACTCGCCC GA    72

( 2 ) INFORMATION FOR SEQ ID NO: 69:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 69:

```
GGGAGGACGA TGCGGCCAGG GTCGGTGTGG GGGTAGTACT ACTTACTTGC      50
GTCTTCAGAC GACTCGCCCG A                                     71
```

( 2 ) INFORMATION FOR SEQ ID NO: 70:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 70:

```
GGGAGGACGA TGCGGCCAGG GTGGGTATGG GGGTAGTGCT ACTTACTTGC      50
GTCTTCAGAC GACTCGCCCG A                                     71
```

( 2 ) INFORMATION FOR SEQ ID NO: 71:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 71:

```
GGGAGGACGA TGCGGCCGGG GTGGGTATGG GGGTGGTGCT ACTTACTTGC      50
GTCTTCAGAC GACTCGCCCG A                                     71
```

( 2 ) INFORMATION FOR SEQ ID NO: 72:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 72:

```
GGGAGGACGA TGCGGCCTGG GTGGGTATGG GGGTGGTGCT ACTTACTTGC      50
GTCTTCAGACG ACTCGCCCG A                                     71
```

( 2 ) INFORMATION FOR SEQ ID NO: 73:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 73:

```
GGGAGGACGA  TGCGGCCACG  GGTGGGTGTG  GGGTAGTGTG  TCTCACTTTA        50

CATCACCAGA  CGACTCGCCC  GA                                        72
```

( 2 ) INFORMATION FOR SEQ ID NO: 74:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 74:

```
GGGAGGACGA  TGCGGCCCGG  GGTGGGTGTG  GGGTAGTGTA  TTATATTTAC        50

AGCCTCAGAC  GACTCGCCCG  A                                         71
```

( 2 ) INFORMATION FOR SEQ ID NO: 75:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 75:

```
GGGAGGACGA  TGCGGCCAGG  GTCGGTGTGG  GGTGGTGTAC  TTTTTCCTGT        50

CCTTCCAGAC  GACTCGCCCG  A                                         71
```

( 2 ) INFORMATION FOR SEQ ID NO: 76:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 76:

```
GGGAGGACGA  TGCGGCCAGG  GTCGGTATGG  GGTAGTGTAC  TTTTTAATGA        50

TCTTCCAGAC  GACTCGCCCG  A                                         71
```

( 2 ) INFORMATION FOR SEQ ID NO: 77:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 77:

```
GGGAGGACGA  TGCGGCCCGG  GGGAGAGCGG  TGGGTAGTGT  TCTATAGTAT        50

TCGTGTCAGA  CGACTCGCCC  GA                                        72
```

( 2 ) INFORMATION FOR SEQ ID NO: 78:

( i ) SEQUENCE CHARACTERISTICS:
        ( A ) LENGTH: 71 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO: 78:

| GGGAGGACGA | TGCGGCCAGG | GGGGGTATGT | TTTAATACT | ACTTACTTAC | 50 |
| GTCTTCAGAC | GACTCGCCCG | A | | | 71 |

( 2 ) INFORMATION FOR SEQ ID NO: 79:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 79:

| GGGAGGACGA | TGCGGCCAGG | GAGGGTATGG | GGGTGGTGTT | TCTAGTTTTG | 50 |
| CGGCGTCAGA | CGACTCGCCC | GA | | | 72 |

( 2 ) INFORMATION FOR SEQ ID NO: 80:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 80:

| GGGAGGACGA | TGCGGCCAGG | GTGGGCATGG | GGGTGGTGTG | GATTAATTCT | 50 |
| TCGTCCCAGA | CGACTCGCCC | GA | | | 72 |

( 2 ) INFORMATION FOR SEQ ID NO: 81:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 81:

| GGGAGGACGA | TGCGGCCAGG | GTCGGTGTGG | GGTGGTGTTT | TTATTTACTC | 50 |
| GTCGCCAGAC | GACTCGCCCG | A | | | 71 |

( 2 ) INFORMATION FOR SEQ ID NO: 82:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 82:

| GGGAGGACGA | TGCGGGGGGC | GGCTTGGAAG | AGGTTGCCGG | TTGGAGTATT | 50 |
| CGAGCCAGAC | GACTCGCCCG | A | | | 71 |

( 2 ) INFORMATION FOR SEQ ID NO: 83:

( i ) SEQUENCE CHARACTERISTICS:
    ( A ) LENGTH: 67 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO: 83:

```
GGGAGGACGA TGCGGCCAGG TGTGGGGTGG TTTGGGTTTT CTTTCGTCGC      50
CCAGACGACT CGCCCGA                                          67
```

( 2 ) INFORMATION FOR SEQ ID NO: 84:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 84:

```
GGGAGGACGA TGCGGCCAGG GTGGGTATGG GGGTTTAATT AATTCTTCGT      50
CCCACAGACG ACTCGCCCGA                                       70
```

( 2 ) INFORMATION FOR SEQ ID NO: 85:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 85:

```
GGGAGGACGA TGCGGGGGGC GGCTTGGAAG AGGTTGCCGG TTGGAGTATT      50
CGAGCCAGAC GACTCGCCCG A                                     71
```

( 2 ) INFORMATION FOR SEQ ID NO: 86:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 86:

```
GGGAGGACGA TGCGGCCGG GGTGGGTGTG GGGTGGTGTG AATTAATTCT       50
TCGTCCCAGA CGACTCGCCC GA                                    72
```

( 2 ) INFORMATION FOR SEQ ID NO: 87:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 87:

```
GGGAGGACGA TGCGGCCCGG GGTGGGTGTG GGGTGGTGTA TTATATTTGC      50
```

GGCCTCAGAC GACTCGCCCG A                                                71

( 2 ) INFORMATION FOR SEQ ID NO: 88:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 88:

GGGAGGACGA TGCGGCCAGG GTCGGTGTGG GTGGTGTACT TTTTCCTGTC          50

CTTCCAGACG ACTCGCCCGA                                          70

( 2 ) INFORMATION FOR SEQ ID NO: 89:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 89:

GGGAGGACGA TGCGGGGGGC GGCTTGGAAG AGGTTGCCGG TTGGAGTATT          50

CGAGCCAGAC GACTCGCCCG A                                        71